United States Patent
Coulombe et al.

(10) Patent No.: US 12,076,437 B2
(45) Date of Patent: Sep. 3, 2024

(54) PROANGIOGENIC PROTEIN COCKTAILS DELIVERED IN CUSTOM BIOMATERIALS TO REVASCULARIZE ISCHEMIC TISSUE

(71) Applicant: Brown University, Providence, RI (US)

(72) Inventors: Kareen L. K. Coulombe, Pawtucket, RI (US); Stephanie Roser, Florham Park, NJ (US); Fabiola Munarin, Smithfield, RI (US); Alicia Minor, Providence, RI (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

(21) Appl. No.: 17/862,962

(22) Filed: Jul. 12, 2022

(65) Prior Publication Data
US 2023/0020862 A1    Jan. 19, 2023

Related U.S. Application Data

(60) Provisional application No. 63/220,865, filed on Jul. 12, 2021, provisional application No. 63/220,859, filed on Jul. 12, 2021.

(51) Int. Cl.
*A61K 9/06* (2006.01)
*A61K 38/18* (2006.01)
(Continued)

(52) U.S. Cl.
CPC ............ *A61K 9/06* (2013.01); *A61K 38/1825* (2013.01); *A61K 38/1858* (2013.01);
(Continued)

(58) Field of Classification Search
CPC ............ A61K 38/1825; A61K 38/1858; A61K 38/1866; A61K 47/36; A61K 47/42; A61K 38/30
See application file for complete search history.

(56) References Cited

U.S. PATENT DOCUMENTS

| 4,377,592 A | 3/1983 | Aurousseau |
| 6,759,386 B2 | 7/2004 | Franco |

(Continued)

FOREIGN PATENT DOCUMENTS

| AU | 2014323098 A1 | 5/2016 |
| CA | 2886396 A1 | 1/2014 |

(Continued)

OTHER PUBLICATIONS

Zuo, Q.; Xue, W. et al. Biomed. Mater. 10 (2015) 035008 (Year: 2015).*

(Continued)

*Primary Examiner* — Andrew D Kosar
*Assistant Examiner* — John D McAnany
(74) *Attorney, Agent, or Firm* — Adler Pollock & Sheehan P.C.

(57) ABSTRACT

The invention provides a highly versatile system to promote vascularization in ischemic tissue. The system is composed of a fully defined, customizable hydrogel loaded with a potent cocktail of proangiogenic growth factors. The hydrogel's mechanical, degradation, and factor release behavior can be tailored to the specifications of any given target tissue or ischemic disease state. The growth factor cocktail can be optimized for maximal vessel density or size to meet the perfusion specifications required by the tissue. The embodiments of the disclosure concern methods and compositions of the system, with examples of preparation for both injectable and implantable delivery modes.

12 Claims, 11 Drawing Sheets

(51) Int. Cl.
    A61K 38/30      (2006.01)
    A61K 47/36      (2006.01)
    A61K 47/42      (2017.01)
(52) U.S. Cl.
    CPC .......... *A61K 38/1866* (2013.01); *A61K 38/30* (2013.01); *A61K 47/36* (2013.01); *A61K 47/42* (2013.01)

(56) References Cited

U.S. PATENT DOCUMENTS

| | | | |
|---|---|---|---|
| 7,125,856 | B1 | 10/2006 | Isner |
| 7,622,299 | B2 | 11/2009 | Sanders et al. |
| 8,318,488 | B1 | 11/2012 | Bohlen et al. |
| 8,492,339 | B2 | 7/2013 | Miller |
| 8,497,252 | B2 | 7/2013 | Hosoda et al. |
| 8,703,483 | B2 | 4/2014 | Cezar |
| 9,085,756 | B2 | 7/2015 | Fisk et al. |
| 9,273,286 | B2 | 3/2016 | Ma |
| 9,303,245 | B2 | 4/2016 | Rivron et al. |
| 9,675,670 | B2 | 6/2017 | Clokie et al. |
| 10,034,738 | B2 | 7/2018 | Thavandiran et al. |
| 10,048,275 | B2 | 8/2018 | Kralj et al. |
| 10,113,150 | B2 | 10/2018 | Wakatsuki |
| 2005/0049287 | A1 | 3/2005 | Ehring et al. |
| 2007/0269476 | A1 | 11/2007 | Voytik-Harbin et al. |
| 2010/0234304 | A1 | 9/2010 | Kirkham et al. |
| 2013/0103079 | A1 | 4/2013 | Lau et al. |
| 2015/0252322 | A1 | 9/2015 | Nain |
| 2015/0283305 | A1 | 10/2015 | Li et al. |
| 2017/0002330 | A1 | 1/2017 | Vunjak-Novakovic et al. |
| 2018/0050130 | A1 | 2/2018 | Jiang et al. |

FOREIGN PATENT DOCUMENTS

| | | | | |
|---|---|---|---|---|
| EP | 2946011 | A1 | * 11/2015 | ............. A61K 35/44 |
| EP | 3063262 | A1 | 9/2016 | |
| WO | 2013056019 | A1 | 4/2013 | |
| WO | 2015158777 | A1 | 10/2015 | |
| WO | 2017093524 | A1 | 6/2017 | |
| WO | 2018013851 | A1 | 1/2018 | |
| WO | 2018195166 | A1 | 10/2018 | |
| WO | 2019106438 | A1 | 6/2019 | |
| WO | 2019126315 | A1 | 6/2019 | |
| WO | 2020113025 | A1 | 6/2020 | |

OTHER PUBLICATIONS

Gonzalez-Pujana, A.; Mooney, D. et al. Biomaterials 257 (2020) 120266 (Year: 2020).*

Son, J.; Park, J. et al. Journal of Visual Experiments (107), e53475, (2016) (Year: 2016).*

Hendrikse, S. I. S.; Meijer, E. W.; Dankers, P. Y. W. "Supramolecular Platform Stabilizing Growth Factors" Biomacromolecules 19, 2610-2617, 2018. (Year: 2018).*

Buikema, et al., "Wnt Activation and Reduced Cell-Cell Contact Synergistically Induce Massive Expansion of Functional Human iPSC-Derived Cardiomyocytes", Cell Stem Cell, vol. 27, Issue 1, Jul. 2, 2020, pp. 50-63.e1-e5.

Burridge, et al., "Chemically Defined Generation of Human Cardiomyocytes", Nature Methods, vol. 11, No. 8, Jun. 15, 2014, 10 pages.

Caves, et al., "Elastin-Like Protein Matrix Reinforced with Collagen Microfibers for Soft Tissue Repair", Biomaterials, vol. 32, No. 23, Aug. 2011, pp. 5371-5379.

Caves, et al., "Fibrillogenesis in Continuously Spun Synthetic Collagen Fiber", Journal of Biomedical Materials Research Part B: Applied Biomaterials, vol. 93, Issue 1, Apr. 2010, pp. 1-31.

Elia, et al., "Stimulation of in Vivo Angiogenesis by in Situ Crosslinked, Dual Growth Factor-Loaded, Glycosaminoglycan Hydrogels", Biomaterials, vol. 31, 2010, pp. 4630-4638.

Gogiraju, et al., "Angiogenic Endothelial Cell Signaling in Cardiac Hypertrophy and Heart Failure", Frontiers in Cardiovascular Medicine, vol. 6, Article 20, Mar. 2019, 21 pages.

Harada, et al., "Basic Fibroblast Growth Factor Improves Myocardial Function in Chronically Ischemic Porcine Hearts", Journal of Clinical Investigation, vol. 94, No. 2, Aug. 1994, pp. 623-630.

Kaiser, et al., "Digital Design and Automated Fabrication of Bespoke Collagen Microfiber Scaffolds", Tissue Engineering Part C: Methods, vol. 25, No. 11, 2019, pp. 687-700.

Kant, et al., "Tissues with Patterned Vessels or Protein Release Induce Vascular Chemotaxis in an In Vitro Platform", Tissue Engineering: Part A. Vol. 27, No. 19-20, 2021, pp. 1290-1304.

Khan, et al., "Fibroblast Growth Factor and Vascular Endothelial Growth Factor Play a Critical Role in Endotheliogenesis from Human Adipose-Derived Stem Cells", Journal of Vascular Surgery, vol. 65, Issue 5, May 2017, pp. 1483-1492.

Kofron, et al., "A Predictive in vitro Risk Assessment Platform for Pro Arrhythmic Toxicity Using Human 3D Cardiac Microtissues", Scientific Reports, vol. 11, No. 10228, 2021, 16 pages.

Lian, et al., "Directed Cardiomyocyte Differentiation from Human Pluripotent Stem Cells by Modulating Wnt/b-Catenin Signaling Under Fully Defined Conditions", Nature Protocols, vol. 8, No. 1, 2013, pp. 162-175.

Liu, et al., "Human Embryonic Stem Cell-Derived Cardiomyocytes Restore Function in Infarcted Hearts of Non-Human Primates", Nature Biotechnology, vol. 36, Issue 7, 2018, pp. 597-605.

Lopez, et al., "Basic Fibroblast Growth Factor in a Porcine Model of Chronic Myocardial Ischemia: A Comparison of Angiographic, Echocardiographic and Coronary Flow Parameters", Journal of Pharmacology and Experimental Therapeutics, vol. 282, No. 1, Jul. 1997, pp. 385-390.

Lu, et al., "Effects of Vascular Endothelial Growth Factor and Insulin Growth Factor 1 on Proliferation, Migration, Osteogenesis and Vascularization of Human Carious Dental Pulp Stem Cells", Molecular Medicine Reports, vol. 20, 2019, pp. 3924-3932.

Menasche, et al., "Transplantation of Human Embryonic Stem Cell-Derived Cardiovascular Progenitors for Severe Ischemic Left Ventricular Dysfunction", Journal of the American College of Cardiology, vol. 71, No. 4, Jan. 30, 2018, pp. 429-438.

Minor, et al., "Abstract P1142: Engineering Vascular Therapies With Angiogenic Factors For Cardiac Regeneration And Tissue Remodeling", Circulation Research, vol. 131, Nov. 14, 2022, 5 pages.

Minor, et al., "Identifying Optimum Combinations of Growth Factors and Cytokines to Maximize Vascular Response in Vivo", Cardiovascular Student Research Symposium, 2021, 15 pages.

Minor, et al., "Identifying Potent Combinations of Angiogenic Factors to Engineer Cardiac Regenerative Therapies", NAVBO, Vasculata Boston,, 2021, 1 page.

Mirabella, et al., "3D-printed Vascular Networks Direct Therapeutic Angiogenesis in Ischaemia", Nature Biomedical Engineering, vol. 1, No. 6, Jun. 13, 2017, 8 pages.

Munarin, et al., "Engineered Human Myocardium with Local Release of Angiogenic Proteins Improves Vascularization and Cardiac Function in Injured Rat Hearts", Biomaterials, vol. 251, No. 120033, Apr. 12, 2020, 15 pages.

Munarin, et al., "Heparin-modified Alginate Microspheres Enhance Neovessel Formation in hiPSC-Derived Endothelial Cells and Heterocellular in Vitro Models by Controlled Release of Vascular Endothelial Growth Factor", Journal of Biomedical Materials Research, vol. 109, Issue 9, Mar. 17, 2021, pp. 1726-1736.

Munarin, et al., "Laser-Etched Designs for Molding Hydrogel-Based Engineered Tissues", Tissue Engineering: Part C, vol. 23, 2017, pp. 311-321.

Reboucas, et al., "Cardiac Regeneration using Growth Factors: Advances and Challenges", Arquivos Brasileiros de Cardiologia, vol. 107, Issue 3, 2016, pp. 271-275.

Romagnuolo, "Human Embryonic Stem Cell-Derived Cardiomyocytes Regenerate the Infarcted Pig Heart but Induce Ventricular Tachyarrhythmias", Stem Cell Reports, vol. 12, No. 5, May 14, 2019., pp. 967-981.

(56) References Cited

OTHER PUBLICATIONS

Roser, et al., "Abstract P1141: Heparinized Alginate And Collagen-based Hydrogels Enhance Localized Vascularization In Ischemic Tissue", Circulation Research, vol. 131, Nov. 14, 2022, 5 pages.
Roser, Stephanie M, "Optimization of Heparinized Alginate-Based Hydrogels to Promote Vascularization in Cardiac Disease", Cardiovascular Student Research Symposium, 2021, 9 pages.
Ruel, et al., "Inhibition of the Cardiac Angiogenic Response to Surgical FGF-2 Therapy in a Swine Endothelial Dysfunction Model", Circulation, vol. 108, Suppl II, Sep. 9, 2003, pp. II-335-11-340.
Rupert, et al., "Human Cardiac Fibroblast No. and Activation State Modulate Electromechanical Function of hiPSC-Cardiomyocytes in Engineered Myocardium", Stem Cells International, vol. 2020, Article ID 9363809, 2020, 16 pages.
Rupert, et al., "Practical Adoption of state-of-the-art hiPSC-cardiomyocyte Differentiation Techniques", PLoS One, vol. 15, Issue 3, e0230001, Mar. 10, 2020, pp. 1-13.
Sack, et al., "Intra-Myocardial Alginate Hydrogel Injection Acts as a Left Ventricular Mid-Wall Constraint in Swine", Acta Biomaterialia, vol. 111, May 30, 2020, pp. 170-180.
Taimeh, et al., "Vascular Endothelial Growth Factor in Heart Failure", Nature Reviews Cardiology, vol. 10, 2013, pp. 519-530.
Virani, et al., "Heart Disease and Stroke Statistics—2021 Update", Circulation, vol. 143, Issue 8, Feb. 23, 2021, pp. e254-e743.
Vo, et al., "The Biomechanics and Optimization of the Needle-Syringe System for Injecting Triamcinolone Acetonide into Keloids", Journal of Medical Engineering, vol. 2016, Article ID 5162394, 2016, 8 pages.
Voisine, et al., "Inhibition of the Cardiac Angiogenic Response to Exogenous Vascular Endothelial Growth Factor", Surgery, vol. 136, No. 2, Aug. 2004, pp. 407-415.
"A Strategic Roadmap for Establishing New Approaches to Evaluate the Safety of Chemicals and Medical Products in the United States", Interagency Coordinating Committee on The Validation of Alternative Methods, Jan. 2018, pp. 441-452.
"Assessment of Pro-Arrhythmic Effects Using Pluricyte.RTM. Cardiomyocytes", on the ACEA xCELLigence® RTCA CardioECR, Mar. 2018, 15 pages.
"High throughput cardiotoxicity assays using stem cell-derived cardiomyocytes", Molecular Devices,, 2015, 3 pages.
"International Search Report and Written Opinion received in International Application No. PCT/US2020/033394, mailed on Aug. 18, 2020", Aug. 18, 2020, 9 pages.
"Preliminary Report: Effect of Encainide and Flecainide on Mortality in a Randomized Trial of Arrhythmia Suppression after Myocardial Infarction", The New England Journal of Medicine (NEJM), vol. 321, No. 6, 1989, pp. 406-412.
"Ranexa: Ranolazine Extended-Release tTblets", CV Therapeutics, NDA 21-526/S-002 Approval Letter, 2006, 13 pages.
Aday, "Epidemiology of Peripheral Artery Disease and Polyvascular Disease", Circulation Research, vol. 128, No. 12, 2021, pp. 1818-1832.
Alinejad, et al., "A systematic Review of the Cardiotoxicity of Methadone", EXCLI Journal, vol. 14, May 5, 2015, pp. 577-600.
Andrae, et al., "Role of Platelet-Derived Growth Factors in Physiology and Medicine", Genes & Development, vol. 22, No. 10, 2008, pp. 1276-1312.
Anversa, et al., "Absolute Morphometric Study of Myocardial Hypertrophy in Experimental Hypertension. II. Ultrastructure of Myocytes and Interstitium", Laboratory Investigation, vol. 38, No. 5, May 1, 1978, pp. 597-609. (Abstract Only).
Anversa, et al., "Stereological Measurement of Cellular and Subcellular Hypertrophy and Hyperplasia in the Papillary Muscle of Adult Rat", Journal of Molecular and Cellular Cardiology (JMCC), vol. 12, No. 8, 1980, pp. 781-795.
Armoundas, et al., "Prognostic Significance of Electrical Alternans Versus Signal Averaged Electrocardiogram Predicting the Outcome of Electrophysiological Testing and Arrhythmia-Free Survival", Heart, vol. 80, 1998, pp. 251-256.
Asazuma-Nakamura, et al., "Cx43 Contributes to TGF-.Beta. Signaling to Regulate Differentiation of Cardiac Fibroblasts into Myofibroblasts", Experimental Cell Research, vol. 315, No. 7, 2009, pp. 1190-1199.
Bashey, et al., "Growth Properties and Biochemical Characterization of Collagens Synthesized by Adult Rat Heart Fibroblasts in Culture", Journal of Molecular and Cellular Cardiology, vol. 24, No. 7, 1992, pp. 691-700.
Beauchamp, et al., "3D Co-culture of hiPSC-Derived Cardiomyocytes With Cardiac Fibroblasts Improves Tissue- Like Features of Cardiac Spheroids", Frontiers in Molecular Biosciences, vol. 7, Article 14, Feb. 2020, 17 pages.
Begley, et al., "Spherical Indentation of Freestanding Circular Thin Films in the Membrane Regime", Journal of the Mechanics and Physics of Solids, vol. 52, 2004, pp. 2005-2023.
Bergmann, et al., "Dynamics of Cell Generation and Turnover in the Human Heart", Cell, vol. 161, No. 7, Jun. 18, 2015, pp. 1566-1575.
Bielawski, et al., "Real-Time Force and Frequency Analysis of Engineered Human Heart Tissue Derived from Induced Pluripotent Stem Cells Using Magnetic Sensing", Tissue Engineering,, 2016, 31 pages.
Blinova, et al., "Comprehensive Translational Assessment of Human-Induced Pluripotent Stem Cell Derived Cardiomyocytes for Evaluating Drug-Induced Arrhythmias", Toxicological Sciences, vol. 155, No. 1, 2017, pp. 234-247.
Blinova, et al., "International Multisite Study of Human-Induced Pluripotent Stem Cell-Derived Cardiomyocytes for Drug Proarrhythmic Potential Assessment", Cell Reports, vol. 24, No. 13, Sep. 25, 2018, pp. 3582-3592.
Brady, et al., "Guided Vascularization In The Rat Heart Leads To Transient Vessel Patterning", APL Bioengineering, vol. 4, 2020, 11 pages.
Burnett, et al., "Human Induced Pluripotent Stem Cell (iPSC)-Derived Cardiomyocytes as an in Vitro Model in Toxicology: Strengths and Weaknesses for Hazard Identification and Risk Characterization", Expert Opinion on Drug Metabolism & Toxicology, vol. 17, No. 8, 2021, pp. 887-902.
Campia, et al., "Peripheral Artery Disease: Past, Present, and Future", The American Journal of Medicine, vol. 132, No. 10, 2019, pp. 1133-1141.
Chen, et al., "Application of the Cell Sheet Technique in Tissue Engineering (Review)", Biomedical Reports, vol. 3, No. 6, 2015, pp. 749-757.
Chong, et al., "Human Embryonic-Stem-Cell-Derived Cardiomyocytes Regenerate Non-Human Primate Hearts", Nature, vol. 510, No. 7504, 2014, pp. 273-277.
Clement, et al., "Expression and Function of .alpha.-Smooth Muscle Actin During Embryonic-Stem-Cell-Derived Ardiomyocyte Differentiation", Journal of Cell Science, vol. 120, No. 2, 2007, pp. 229-238.
Colatsky, et al., "The Comprehensive in Vitro Proarrhythmia Assay (CiPA) Initiative—Update on Progress", Journal of Pharmacological and Toxicological Methods, vol. 81, 2016, pp. 15-20.
Cyganek, et al., "Deep Phenotyping of Human Induced Pluripotent Stem Cell-Derived Atrial and Ventricular Cardiomyocytes", JCI Insight, vol. 3, No. 12, e99941, Jun. 21, 2018, 17 pages.
Desai, et al., "Reversible Modulation of Myofibroblast Differentiation in Adipose-Derived Mesenchymal Stem Cells", PLOS One, vol. 9, Issue 1, Jan. 2014, 12 pages.
Doble, et al., "Basic Fibroblast Growth Factor Stimulates connexin-43 Expression and Intercellular Communication of Cardiac Fibroblasts", Molecular and Cellular Biochemistry, vol. 143, No. 1, 1995, pp. 81-87.
Dolnikov, et al., "Functional Properties of Human Embryonic Stem Cell-Derived Cardiomyocytes: Interacellular Ca2? Handling and the ROle of Sarcoplasmic Reticulum in the Contraction", Cells, vol. 21, No. 2, 2006, pp. 236-245.
Domenech, et al., "Tissue Engineering Strategies for Myocardial Regeneration: Acellular Versus Cellular Scaffolds?", Tissue Engineering. Part B, vol. 22, No. 6, 2016, pp. 438-458.

(56) References Cited

OTHER PUBLICATIONS

Dutta, et al., "Optimization of an In silico Cardiac Cell Model for Proarrhythmia Risk Assessment", Frontiers in Physiology, vol. 8, Article 616, Aug. 23, 2017, pp. 1-15.
Efimov, et al., "Optical Mapping of Repolarization and Refractoriness from Intact Hearts", Circulation, vol. 90, No. 3, Sep. 1994, pp. 1469-1480.
Eghbali, et al., "Localization of Types I, III and IV Collagen mRNAs in Rat Heart Cells by in situ Hybridization", Journal of Molecular and Cellular Cardiology, vol. 21, No. 1, 1989, pp. 103-113.
Evans, et al., "TGF-.beta.1-Mediated Fibroblast-Myofibroblast Terminal Differentiation—The Role of Smad Proteins", Experimental Cell Research, vol. 282, 2003, pp. 90-100.
Fahrenbach, et al., "The Relevance of Non-Excitable Cells for Cardiac Pacemaker Function", Journal of Physiology, vol. 585.2, Oct. 4, 2007, pp. 565-578.
Fassbender, Melissa, "The Global Market for in Vitro Toxicity Testing is Predicted to Reach $8.Sbn by 2023", Accsses through "https://www.outsourcing-pharma.com/Article/2018/08/02/Global-in-vitro-toxicity-testing-market-to-reach-8.8bn-by-2023", Aug. 2, 2018, 3 pages.
Fenichel, et al., "Drug-Induced Torsade de Pointes and Implications for Drug Development", Journal of Cardiovascular Electrophysiology (JCE), vol. 15, No. 4, 2004, pp. 475-495.
Ferdinandy, et al., "Definition of Hidden Drug Cardiotoxicity: Paradigmchange in Cardiac Safety Testing and its Clinical Implications", European Heart Journal, 2018, pp. 1-10.
Feric, et al., "Engineered Cardiac Tissues Generated in the Biowire II: A Platform for Human-Based Drug Discovery", Toxicological Sciences, vol. 172, No. 1, 2019, pp. 89-97.
Ferrara, et al., "The Biology of VEGF and its Receptors", Nature Medicine, vol. 9, No. 6, Jun. 2003, pp. 669-676.
Gao, et al., "Impact of Bisphenol A on the Cardiovascular System—Epidemiological and Experimental Evidence and Molecular Mechanisms", International Journal of Environmental Research and Public Health, vol. 11, No. 8, 2014, pp. 8399-8413.
Gerbin, et al., "Enhanced Electrical Integration of Engineered Human Myocardium via Intramyocardial versus Epicardial Delivery in Infarcted Rat Hearts", PLoS One, vol. 10, No. 7, e0131446, Jul. 10, 2015, pp. 1-20.
Granato, et al., "Generation and Analysis of Spheroids from Human Primary Skin Myofibroblasts: An Experimental System to Study Myofibroblasts Deactivation", Cell Death Discovery, vol. 3, No. 17038, Jul. 17, 2017, 10 pages.
Grimm, et al., "A Human Population-Based Organotypic in Vitro Model for Cardiotoxicity Screening", Altex, vol. 35, No. 4, 2018, pp. 441-452.
Weyers, et al., "Retrograde perfusion and filling of mouse coronary vasculature as preparation for micro computed tomography imaging", J Vis Exp, vol. 60, 2021, pp. 3740.
Weyers, et al., "Sonic Hedgehog Upregulation Does Not Enhance The Survival And Engraftment Of Stem Cell-Derived Cardiomyocytes In Infarcted Hearts", PLOS One, vol. 15, 2019, 20 pages.
White, et al., "Implanted Cell-Dense Prevascularized Tissues Develop Functional Vasculature That Supports Reoxygenation After Thrombosis", Tissue Engineering: Part A, vol. 20, No. 17-18, 2014, pp. 2316-2328.
Hayakawa, et al., "Noninvasive Evaluation of Contractile Behavior of Cardiomyocyte Monolayers Based on Motion Vector Analysis", Tissue Engineering: Part C, vol. 18, No. 1, Jan. 1, 2012, pp. 21-32.
Heranval, et al., "Drugs with Potential Cardiac Adverse Effects: Retrospective Study in a Large Cohort of Parkinsonian Patients", Revue Neurologique, vol. 172, No. 4-5, 2016, pp. 318-323.
Herper, Matthew, "The Truly Staggering Cost Of Inventing New Drugs", Accessed through "https://www.forbes.com/sites/matthewherper/2012/02/10/the-truly-staggering-cost-of-inventing-new-drugs/?sh=17dbe6bb4a94", Feb. 10, 2012, 5 pages.
Hirt, et al., "Cardiac Tissue Engineering: State of the Art", Circulation Research, vol. 114, 2014, pp. 354-367.
Huang, et al., "Matrix Stiffness-Induced Myofibroblast Differentiation Is Mediated by Intrinsic Mechanotransduction", American Journal of Respiratory Cell and Molecular Biology, vol. 47, Issue 3, Sep. 2012, pp. 340-348.
Ivey, et al., "Defining the Cardiac Fibroblast", Circulation Journal, vol. 80, No. 11, Nov. 2016, pp. 2269-2276.
Jackman, et al., "Engineered Cardiac Tissue Patch Maintains Structural and Electrical Properties After Epicardial Implantation", Biomaterials, vol. 159, 2018, pp. 48-58.
Jin, et al., "Dynamic Fracture of a Bicontinuously Nanostructured Copolymer: A Deep-Learning Analysis of Big-Data-Generating Experiment", Journal of the Mechanics and Physics of Solids, vol. 164, 2022, pp. 1-22.
Johannesen, et al., "Differentiating Drug-Induced Multichannel Block on the Electrocardiogram: Randomized Study of Dofetilide, Quinidine, Ranolazine, and Verapamil", Clinical pharmacology & Therapeutics, vol. 96, No. 5, Nov. 2014, pp. 549-558.
Johannesen, et al., "Late Sodium Current Block for Drug-Induced Long QT Syndrome: Results From a Prospective Clinical Trial", Clinical Pharmacology & Therapeutics, vol. 99, No. 2, 2016, pp. 214-223.
Kaiser, et al., "Custom Engineered Tissue Culture Molds from Laser-etched Masters", Journal of Visualized Experiments, vol. 135, e57239, 2018, pp. 1-7.
Kant, et al., "Integrated approaches to spatiotemporally directing angiogenesis in host and engineered tissues", Acta Biomater, vol. 69, 2018, pp. 42-62.
Kant, et al., "Patterned Arteriole-Scale Vessels Enhance Engraftment, Perfusion, and Vessel Branching Hierarchy of Engineered Human Myocardium for Heart Regeneration", Cells, vol. 12,, 2023, 26 pages.
Kofron, et al., "Gq-Activated Fibroblasts Induce Cardiomyocyte Action Potential Prolongation and Automaticity in a 3D Microtissue Environment", American Journal of Physiology-Heart and Circulatory Physiology, vol. 313, No. 4, Jul. 14, 2017, 41 pages.
Kollmannsberger, et al., "Tensile Forces Drive a Reversible Fibroblast-To-Myofibroblast Transition During Tissue Growth in Engineered Clefts", Science Advances, vol. 4, No. 1, eaao4881, Jan. 17, 2018, pp. 1-10.
Kreutziger, et al., "Developing Vasculature and Stroma in Engineered Human Myocardium", Tissue Engineering: Part A, vol. 17, Nos. 9 and 10, 2011, pp. 1219-1228.
Lemoine, et al., "Human Induced Pluripotent Stem Cell-Derived Engineered Heart Tissue as a Sensitive Test System for QT Prolongation and Arrhythmic Triggers", Circulation: Arrhythmia and Electrophysiology, vol. 11, e006035., Jul. 2018, 15 pages.
Lemoine, et al., "Human iPSC-Derived Cardiomyocytes Cultured in 3D Engineered Heart Tissue Show Physiological Upstroke Velocity and Sodium Current Density", Scientific Reports, vol. 7, Article No. 5464, 2017, 13 pages.
Livak, et al., "Analysis of Relative Gene Expression Data Using Real-Time Quantitative PCR and the 2-ΔΔCT Method", Methods, vol. 25, 2001, pp. 402-408.
Makarenko, et al., "Passive Stiffness Changes Caused by Upregulation of Compliant Titin Isoforms in Human Dilated Cardiomyopathy Hearts", Circulation Research, vol. 95, No. 7, 2004, pp. 708-716.
Mason, et al., "Electrocardiogramce Ranges Derived from 79,743 Ambulatory Subjects", Journal of Electrocardiology, vol. 40, No. 3, 2007, pp. 228-234e8.
McKim, Jr., et al., "Building a Tiered Approach to In Vitro Predictive Toxicity Screening: A Focus on Assays with In Vivo Relevance", Combinatorial Chemistry & High Throughput Screening, vol. 13, No. 2, 2010, pp. 188-206.
Miragoli, et al., "Electrotonic Modulation of Cardiac Impulse Conduction by Myofibroblasts", Circulation Research, vol. 98, No. 6, 2006, pp. 801-810.
Nishimura, et al., "Formation Of Vessel-Like Channel Using Alginate Fiber As A Sacrificial Structure", Proc. IEEE Int. Conf. Micro Electro Mech. Syst. (MEMS), 2017, pp. 596-599.
Niu, et al., "Vascular Endothelial Growth Factor as an Anti-angiogenic Target for Cancer Therapy", Current Drug Targets, vol. 11, No. 8, Aug. 2010, pp. 1000-1017.

(56) References Cited

OTHER PUBLICATIONS

Novosel, et al., "Vascularization is the Key Challenge in Tissue Engineering", Advanced Drug Delivery Reviews, vol. 63, 2011, pp. 300-311.
O'Hara, et al., "Simulation of the Undiseased Human Cardiac Ventricular Action Potential: Model Formulation and Experimental Validation", PLoS Computational Biology, vol. 7, Issue 5, e1002061, May 2011, 29 pages.
O'Reilly, et al., "Bisphenol A Binds to the Local Anesthetic Receptor Site to Block the Human Cardiac Sodium Channel", PLoS One, vol. 7, Issue 1, e41667, Jul. 27, 2012, pp. 1-11.
Okur, et al., "Quantitative Evaluation of Ischemic Myocardial Scar Tissue By Unenhanced T1 Mapping Using 3.0 Tesla MR Scanner", Diagn Interv Radiol, vol. 20, Jun. 18, 2014, pp. 407-413.
Onakpoya, et al., "Post-Marketing Withdrawal of 462 Medicinal Products Because of Adverse Drug Reactions: A Systematic Review of the World Literature", BMC Medicine, vol. 14, No. 10, 2016, pp. 1-11.
Onakpoya, et al., "Worldwide Withdrawal of medicinal products because of adverse drug reactions: a systematic Review and Analysis", Critical Reviews in Toxicology, vol. 46, No. 6, 2016, pp. 477-489.
Peterson, et al., "Overview of Drug Development and Statistical Tools for Manufacturing and Testing", Chapter 15, Nonclinical Statistics for Pharmaceutical and Biotechnology Industries, 2016, pp. 383-414.
Pola, et al., "The Morphogen Sonic Hedgehog is an Indirect Angiogenic Agent Upregulating Two Families of Angiogenic Growth Factors", Nature Medicine, vol. 7, No. 6, Jun. 2001, pp. 706-711.
Posnack, et al., "The Adverse Cardiac Effects of Di(2-ethylhexyl)phthalate and Bisphenol A", Cardiovascular Toxicology, vol. 14, No. 4, May 9, 2014, pp. 339-357.
Quinn, et al., "Electrotonic Coupling of Excitable and Nonexcitable Cells in the Heart Revealed by Optogenetics", Proceedings of the National Academy of Sciences (PNAS), vol. 113, No. 51, 2016, pp. 14852-14857.
Ramalho, et al., "Drug-induced Life-Threatening Arrhythmias and Sudden Cardiac Death: A Clinical Perspective of Long QT, short QT and Brugada Syndromes", Portuguese Journal of Cardiology, vol. 37, No. 5, 2018, pp. 435-446.
Redd, et al., "Patterned Human Microvascular Grafts Enable Rapid Vascularization And Increase Perfusion In Infarcted Rat Hearts", Nature Communications, vol. 10, 2019, 14 pages.
Redfern, et al., "Impact and Frequency of Different Toxicities Throughout the Pharmaceutical Life Cycle", The Toxicologist, e29, 2010, 1 page. (Abstract Only).
Riegler, et al., "Human Engineered Heart Muscles Engraft and Survive Long-Term in a Rodent Myocardial Infarction Model", Circulation Research, vol. 117, Issue 8, Sep. 25, 2015, pp. 720-730.
Rinn, et al., "Anatomic Demarcation by Positional Variation in Fibroblast Gene Expression Programs", PLoS Genetics, vol. 2, Issue 7, Jul. 2006, pp. 1084-1096.
Rook, et al., "Differences in Gap Junction Channels Between Cardiac Myocytes, Fibroblasts, and Heterologous Pairs", American Journal of Physiology-Cell Physiology, vol. 263, No. 5, 1992, pp. C959-C977.
Rook, et al., "Single Channel Currents of Homo- and Heterologous Gap Junctions Between Cardiac Fibroblasts and Myocytes", Pflfigers Arch, vol. 414, No. 1, 1989, pp. 95-98.
Roser, Stephanie M., "Heparinized-Alginate Based Hydrogels for Revascularization in Ischemic Cardiac Disease", Thesis, Submitted in the Graduate Program of Biomedical Engineering at Brown University, May 2022, 50 pages.
Ruan, et al., "Mechanical Stress Conditioning and Electrical Stimulation Promote Contractility and Force Maturation of Induced Pluripotent Stem Cell-Derived Human Cardiac Tissue", Circulation, vol. 134, Issue 20, Nov. 15, 2016, pp. 1557-1567.
Rubart, et al., "Electrical Coupling Between Ventricular Myocytes and Myofibroblasts in the Infarcted Mouse Heart", Cardiovascular Research, vol. 114, No. 3, 2017, 12 pages.
Rupert, et al., "Hypertrophy Changes 3D Shape of hiPSC-Cardiomyocytes: Implications for Cellular Maturation in Regenerative Medicine", Cellular and Molecular Bioengineering, vol. 10, No. 1, Aug. 3, 2016, pp. 54-62.
Rupert, et al., "IGF1 and NRG1 Enhance Proliferation, Metabolic Maturity, and the Force-Frequency Response in hESC-Derived Engineered Cardiac Tissues", Stem Cells International, vol. 2017, Article ID 7648409, 2017, 13 pages.
Rupert, et al., "The Roles of Neuregulin-1 in Cardiac Development, Homeostasis, and Disease", Biomark Insights, vol. 10 (Suppl 1), 2015, pp. 1-9.
Sager, et al., "Rechanneling the Cardiac Proarrhythmia Safety Paradigm: A Meeting Report from the Cardiac Safety Research Consortium", Cardiac Safety Research Consortium, American Heart Journal, vol. 167, No. 3, Mar. 2014, pp. 292-300.
Sekine, et al., "Endothelial Cell Coculture Within Tissue-Engineered Cardiomyocyte Sheets Enhances Neovascularization and Improves Cardiac Function of Ischemic Hearts", Circulation, vol. 118, (14_suppl_1),, Mar. 7, 2015, pp. S145-S152.
Serrao, et al., "Myocyte-Depleted Engineered Cardiac Tissues Support Therapeutic Potential of Mesenchymal Stem Cells", Tissue Engineering: Part A, vol. 18, Nos. 13 and 14, 2012, pp. 1322-1333.
Shah, et al., "influence of Inherent Mechanophenotype on Competitive Cellular Adherence", Annals of Biomedical Engineering, vol. 45, No. 8, Aug. 2017, pp. 2036-2047.
Shinde, et al., "The Role of α-Smooth Muscle Actin in Fibroblast-Mediated Matrix Contraction and Remodeling", Biochimica et Biophysica Acta, vol. 1863, No. 1, 2017, pp. 298-309.
Soepriatna, et al., "Human Atrial Cardiac Microtissues for Chamber-Specific Arrhythmic Risk Assessment", Cell Mol Bioeng, vol. 14, No. 5, 2021, pp. 441-457.
Sousa, et al., "Smooth Muscle a-Actin Expression and Myofibroblast Differentiation by TGFb are Dependent Upon MK2", Journal of Cellular Biochemistry, vol. 100, No. 6, 2007, pp. 1581-1592.
Strauss, et al., "Comprehensive In Vitro Proarrhythmia Assay (CiPA) Update from a Cardiac Safety Research Consortium / Health and Environmental Sciences Institute / FDA Meeting", Therapeutic Innovation & Regulatory Science, vol. 53, No. 4, 2019, pp. 519-525.
Sullivan, et al., "Extracellular Matrix Remodeling Following Myocardial Infarction Influences the Therapeutic Potential of Mesenchymal Stem Cells", Stem Cell Research & Therapy, vol. 5, No. 14, 2014, pp. 1-15.
Sun, et al., "Brugada-Type Pattern on Electrocardiogram Associated with High-Dose Loperamide Abuse", The Journal of Emergency Medicine, vol. 54, No. 4, 2018, pp. 484-486.
Surawicz, et al., "Cardiac Alternans: Diverse Mechanisms and Clinical Manifestations", Journals of the American College of Cardiology (JACC), vol. 20, No. 2, Aug. 1992, pp. 483-499.
Tandon, et al., "Electrical Stimulation Systems for Cardiac Tissue Engineering", Nature Protocols, vol. 4, No. 2, Jan. 22, 2009, pp. 155-173.
Tiburcy, et al., "Defined Engineered Human Myocardium With Advanced Maturation for Applications in Heart Failure Modeling and Repair", Circulation, vol. 135, Issue 19, May 9, 2017, pp. 1832-1847.
Tohyama, et al., "Distinct Metabolic Flow Enables Large-Scale Purification of Mouse and Human Pluripotent Stem Cell-Derived Cardiomyocytes", Cell Stem Cell, vol. 12, Jan. 3, 2013, pp. 127-137.
Verkerk, et al., "Patch-Clamp Recording from Human Induced Pluripotent Stem Cell-Derived Cardiomyocytes: Improving Action Potential Characteristics through Dynamic Clamp", International Journal of Molecular Sciences, vol. 18, No. 9, 2017, pp. 1-23.
Vollert, et al., "In Vitro Perfusion of Engineered Heart Tissue Through Endothelialized Channels", Tissue Engineering Part A, vol. 20, No. 3-4, 2014, pp. 854-863.
Vozenin, et al., "The Myofibroblast Markers -SM actin and B-actin are Differentially Expressed in 2 and 3-D Culture Models of Fibrotic and Normal Skin", Cytotechnology, vol. 26, No. 1, 1998, pp. 29-38.
Waldo, et al., "Effect of d-sotalol on Mortality in Patients with left ventricular Dysfunction after Recent and Remote Myocardial Infarction", Lancet, vol. 348, No. 1, 1996, pp. 7-12.

(56) References Cited

OTHER PUBLICATIONS

Walsh, et al., "β-adrenergic Modulation of Cardiac Ion Channels: Differential Temperature Sensitivity of Potassium and Calcium Currents", Journal of General Physiology, vol. 93, No. 5, 1989, pp. 841-854.

Wendel, et al., "Functional Effects of a Tissue-Engineered Cardiac Patch From Human Induced Pluripotent Stem Cell-Derived Cardiomyocytes in a Rat Infarct Model", Stem Cells Translational Medicine, vol. 4, No. 11, Sep. 14, 2015, pp. 1324-1332.

Williams, et al., "A 3-D Human Model of Complex Cardiac ArrythmeiasA Platform for Generation of Chamber SPecific Cardiac Tissues and Disease Modeling Cardia", Acta Biomater, vol. 132, Sep. 15, 2021, 31 pages.

Yan, et al., "Bisphenol A and 17b-Estradiol Promote Arrhythmia in the Female Heart via Alteration of Calcium Handling", PLoS One, vol. 6, Issue 9, Sep. 2011, pp. 1-9.

Zhang, et al., "Generation of Quiescent Cardiac Fibroblasts From Human Induced Pluripotent Stem Cells for In Vitro Modeling of Cardiac Fibrosis", Circulation Research, vol. 125, No. 5, 2019, pp. 552-566.

Zhao, et al., "A Multimaterial Microphysiological Platform Enabled by Rapid Casting of Elastic Microwires", Advanced Healthcare Materials, vol. 8, No. 5, e1801187, 2019, pp. 1-10.

Zhao, et al., "A Platform Generation of Chamber-Specific Cardiac Tissues and Disease Modeling", Cell, vol. 176, No. 4, Feb. 7, 2019, pp. 913-927.

Zhou, et al., "Characterization and Standardization of Cultured Cardiac Fibroblasts for ex vivo Models of Heart Fibrosis and Heart Ischemia", Tissue Eng Part C Methods, vol. 12, No. 8, 2017, 43 pages.

Zhou, et al., "Recounting Cardiac Cellular Composition", Circulation Research, vol. 118, No. 3, Mar. 2, 2016, pp. 368-370.

"MicroTissues® 3D Petri Dish® micro-mold Tech Evaluation kit", Millipore Sigma Catalog No. Z764116, 2019, pp. 1-3.

Nunes, et al., "Biowire: A Platform for Maturation of Human Pluripotent Stem Cell-Derived Cardiomyocytes", Nature Methods, vol. 10, 2013, pp. 781-787.

Saini, et al., "3D Cardiac Microtissues Encapsulated With The Co-Culture Of Cardiomyocytes And Cardiac Fibroblasts", Advanced Healthcare Materials, vol. 4, 2015, pp. 1961-1971.

Yang, et al., "Materials Stiffness-Dependent Redox Metabolic Reprogramming of Mesenchymal Stem Cells for Secretome-Based Therapeutic Angiogenesis", Advanced Healthcare Materials, vol. 8, 1900929, 2019, pp. 1-12.

\* cited by examiner

PROANGIOGENIC PROTEIN COCKTAILS DELIVERED IN CUSTOM BIOMATERIALS TO REVASCULARIZE ISCHEMIC TISSUE

CROSS-REFERENCE TO RELATED APPLICATIONS

This patent application claims priority under 35 U.S.C. § 119(e) to the provisional patent applications U.S. Ser. Nos. 63/220,865 and 63/220,859, both filed Jul. 12, 2021, the contents of which are incorporated by reference.

STATEMENT REGARDING FEDERALLY SPONSORED RESEARCH OR DEVELOPMENT

This invention was made with government support under grant number ROI HL135091, awarded by the National Institutes of Health. The government has certain rights in the invention.

TECHNICAL FIELD OF THE INVENTION

This invention generally relates to replacement or repair of human tissue through vascularization, and particularly to use of heparinized-alginate-co-collagen biomaterials for delivery of vasculogenic factors.

BACKGROUND OF THE INVENTION

Cardiovascular disease (CVD) is a major health burden and a contributing factor for myocardial infarction (heart attack), causing local ischemia and cell death in the heart wall. This cardiovascular disease class includes many cardiac diseases and afflictions, each with its own pathology and subsequent treatment requirements. Heart disease is the leading cause of death in the United States, responsible for approximately one in every three deaths. Other conditions such as liver ischemia and peripheral artery disease also lead to temporary or chronic ischemia resulting from lack of blood flow which can have long-term consequences if intervention does not salvage and revascularize surviving tissue.

Regenerative therapeutics provides a set of methods to restore function or replace ischemic tissue. Revascularization can be achieved using growth factors to recapitulate native developmental and wound healing cascades to stimulate angiogenesis and arteriogenesis, helping to form a more robust perfused vasculature. The pro-vasculogenic cocktails identified can increase the efficacy and translatability of regenerative therapeutics for clinical uses.

There remains a need in cardiac regenerative medicine and the tissue engineering art to promote localized new vessel growth and meet the metabolic demands of host or engineered tissue by combining cells from the body with highly porous scaffold biomaterials, which act as templates for tissue regeneration, to guide the growth of new tissue.

SUMMARY OF THE INVENTION

The invention provides a gel composed of heparinized alginate in the first embodiment. Two delivery mechanisms, intramyocardial injection and epicardial implantation are provided.

In a second embodiment, the invention provides a gel composed of heparinized alginate manufactured by a method comprising the steps of beginning with 2% heparin-alginate, then adding 3 mg/mL collagen, then a 0.1-1 M $CaCl_2$ bath to modulate stiffness. The utility of this embodiment, optimized from a compositional range with applicability to several delivery modalities, is an ultra-thin surgically implanted hydrogel film. The handleability and minimal thickness allow co-implantation with engineered tissues to offer localized, controlled, and sustained release of pro-vascularization factors while protecting the biologics from degradation for optimal integration and longevity of the tissue.

In a third embodiment, the $CaCl_2$ bath is 0.15 M.

In a fourth embodiment, the 2% heparin-alginate is formed by obtaining a 4% sodium alginate solution (4 g/100 mL sodium alginate in deionized water) made, sterilized, and used to reach the final desired concentration of alginate.

In a fifth embodiment, 1/10th of the alginate mass (0.4%) is added in the heparinized form from previously functionalized and lyophilized heparin-alginate. The final formulations have 1/10 heparinized-alginate.

In the sixth embodiment, the formulation is then combined with a high concentration of up to 13 mg/mL collagen (isolated from rat tail tendon, human cadaveric tendon, bovine tendon, or other sources) and HEPES buffer.

In a seventh embodiment, persons having ordinary skill in the biomedical art mix and neutralize via adding NaOH until a neutral pH of 7.0 is reached. After properly neutralized, sterile $H_2O$ (when gels are unloaded) or reconstituted growth factors (in appropriate concentration or mass and defined combination when making gels loaded with factors) are added to reach the final target volume, providing final concentrations of 2% alginate, 0.2% heparinized alginate, 3 mg/mL collagen, and 1% HEPES buffer.

In an eighth embodiment, persons having ordinary skill in the biomedical art then pipette into a porous nylon mesh or paper frame on a hydrophilic surface to leverage the surface wetting and integration with the frame for optimal thinness and handleability.

In a ninth embodiment, persons having ordinary skill in the biomedical art then carefully cover with 0.15 M $CaCl_2$ for ten minutes, remove from the cross-linking bath, rinse in DPBS for two minutes and store hydrated for transport and use.

In a tenth embodiment, the invention provides a gel composed of heparinized alginate manufactured by a method comprising the steps of beginning with 1% heparin-alginate, then adding 1 mg/mL collagen, then $CaCO_3$ (about 5 mg/mL). The utility of this embodiment is a biomaterial that can be injected by a needle into a site of interest to locally deliver and release the factors in the biomaterial. The system's versatility beyond these uses speaks to an even greater need, spanning the ranges of cardiac disease and other vascular and ischemic diseases. In the optimized and characterized uses alone, for example, two distinct yet similarly high-incidence cardiac diseases, pulmonary hypertension and myocardial infarction, are addressed.

In an eleventh embodiment, 2% alginate solution (2 g/100 mL sodium alginate in mH2O) with 0.2% (200 mg/100 mL) lyophilized heparinized alginate is combined with 13 mg/mL isolated collagen.

In a twelfth embodiment, sterile mH2O (unloaded) or reconstituted growth factors (loaded by mass from stock solutions with high concentrations) are mixed in.

In a thirteenth embodiment, calcium carbonate (CaCO3) solution is then mixed in the remaining volume to produce a final concentration of about 5 mg/mL CaCO3 and to produce final concentrations of 1% alginate, 1% heparinized alginate, and 1 mg/mL collagen.

In a fourteenth embodiment, the mixture is then quickly loaded into a syringe (polymerization will slowly begin immediately following the addition of the calcium carbonate).

In a fifteenth embodiment, formulating and mixing can be completed in the syringe to minimize volume loss as polymerization begins.

In a sixteenth embodiment, the invention provides a gel composed of heparinized alginate further comprising VEGF, bFGF, Shh, PDGF, and IGF-1. Combinations of proteins and growth factors can be delivered via local injection or implantation and incorporated into a biomaterial to prolong release over time to achieve revascularization in a desired local region of the body. Clinicians and research scientists can use these proangiogenic and pro-vasculogenic cocktails to improve vascular response in vivo and develop targeted engineered therapeutics for clinical uses.

Several growth factors and cytokines are involved in angiogenesis in vivo. Utilizing a Design of Experiments approach, the inventors screened ten factors: vascular endothelial growth factor (VEGF), basic fibroblast growth factor (bFGF), sonic hedgehog (Shh), platelet-derived growth factor (PDGF), insulin-like growth factor-1 (IGF-1), transforming growth factor beta-1 (TGF-$\beta$1), heparin-binding epidermal growth factor (EGF), angiopoietin I (Ang-I), monocyte chemoattractant protein I (MCP-1), and matrix metalloproteinase 9 (MMP-9) for their ability to direct cell migration and vessel formation in vivo. The inventors delivered these growth factors in subcutaneous Matrigel implants and quantified hemoglobin content, lumen formation, cell migration, and vessel perfusion via immunohistochemistry after seven days. The results support the use of five growth factors.

Based on the intended use, one, two, or up to five growth factors are loaded into the biomaterial for vascular growth, remodeling, and regeneration applications. The inventors used these formulations: In rat hearts, 4 g per growth factor is used in small films or injectable formulations. In the pig heart, 425 µg per growth factor is loaded into the biomaterial.

In a seventeenth embodiment, the invention provides a method of delivering VEGF, bFGF, Shh, PDGF, and IGF-1 to a subject. The invention provides for the therapeutic use of five growth factors (VEGF, bFGF, Shh, PDGF, and IGF-1) in combinations at high and low doses to achieve a potent vascular response in vivo.

The inventors identified significant two-factor interactions that elicit net positive or net negative effects on angiogenesis which can inform the selection of proteins for tissue engineering and revascularization therapies.

One advantage of the invention is that the biocompatible materials (most of which are already FDA-approved) have a high loading capacity for protein. Another advantage of the invention is the ubiquitous focus on biological, clinical, and surgical relevance at every step of its design. In each investigated use, both injection and implantation, care was taken to meet the needs of the surgical setting. Biomaterial function was assessed assuming several hours of surgical prep-time, ensuring no significant decrease in performance after sitting at room temperature for up to six hours.

These protein cocktails of VEGF, bFGF, Shh, PDGF, and/or IGF-1 can also be delivered in customized biomaterials made of alginate, chemically modified alginate, collagen, and other biocompatible materials of natural and synthetic origins.

Another advantage of the invention is its versatile use in various indications. Besides its co-implantation with engineered cardiac tissues following a heart attack or when heart failure progression reduces therapeutic options, the composition can be optimized for implantation to induce vascularization of the native tissue or injection into the target tissue, such as the heart wall.

In another advantage of the invention, the product is optimized with a focus on relevance to the clinical, surgical setting. The product can be used by surgeons in patients that have experienced a heart attack or suffer from other ischemic diseases.

BRIEF DESCRIPTION OF THE DRAWINGS

For illustration, some embodiments of the invention are shown in the drawings described below. Like numerals in the drawings indicate like elements throughout. The invention is not limited to the precise arrangements, dimensions, and instruments shown.

FIG. 5A is a bar graph of human cardiomyocyte graft size. Engraftment by cTnT$^+$ area normalized to day 0 implants shows stable engraftment up to day 30 for implants with only hiPSC-CMs ("cells only"), hiPSC-CMs plus alginate microspheres with no protein ("unloaded"), and hiPSC-CMs plus alginate microspheres loaded with a cocktail of angiogenic proteins VEGF+bFGF+Shh ("loaded"). NA is not applicable (no animals were sacrificed in this group on day 7). FIG. 5B shows echocardiography data for whole heart function. Fractional shortening (% FS) shows improved contractility at thirty days in unloaded and loaded treatment groups. FIG. 5C shows a two-dimensional vessel density by immunohistochemical analysis. CD31$^+$ vessel lumens (count/area) normalized to remote region density increases for the loaded vs. cells only group in both the infarct and implant regions. FIG. 5D is three-dimensional (3D) volumetric vessel density by perfused vessel reconstruction after microcomputed tomography imaging. The 3D vessel network is quantified for vessels per volume.

DETAILED DESCRIPTION OF THE INVENTION

Industrial Applicability

Figure 1:
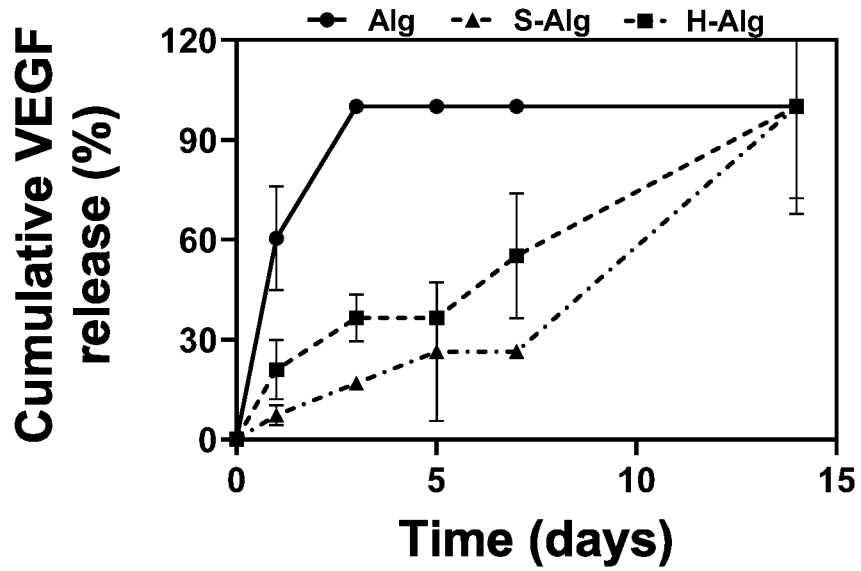
FIG. 1 is a line graph showing that heparin functionalization improves factor binding and retention using an alginate-based proangiogenic factor delivery. See Munarin et al., Biomaterials, 251, 120033 (2020). The insert is an image of a heparinized alginate-based hydrogel.

Ischemic heart disease (IHD) remains the leading cause of years of lost life and mortality for many decades in the United States. See Virani et al., Circulation, 143(8), e254-e743 (2021). The leading cause of death is coronary heart disease, which manifests as either slow onset ischemia due to atherosclerotic narrowing of the arteries or a sudden blockage causing a heart attack (myocardial infarction). The ischemia that results from reduced blood flow causes the death of some cardiomyocytes and impairs the contractile function of surviving cardiomyocytes. Treatments including angioplasty, stenting, and bypass surgery aim to restore blood flow and minimize ongoing damage. Still, they do not address the irreversible loss of cardiomyocytes or facilitate new vessel growth to increase tissue perfusion. Patients prescribed drugs to support cardiac output may respond favorably, at least for some time. Still, many either do not respond or lose responsiveness overtime, precipitating a progressive decline in cardiac function, leading to heart failure. Until advanced heart failure sets in and the patient becomes eligible for implantation of an assistive device or a heart transplant, no therapy currently exists to restore the native heart function in ischemic heart disease patients.

Cardiovascular regenerative medicine depends on stimulating blood vessel development for recovering tissue perfusion and modulating ventricular remodeling. The delivery of angiogenic growth factors and cytokines demonstrated the ability to initiate angiogenesis and vascular network formation in cardiac tissue.

Combinations of proteins and growth factors can be delivered via local injection or implantation and incorporated into a biomaterial to prolong release over time to achieve revascularization in a desired local region of the body. Clinicians and research scientists can use these proangiogenic and pro-vasculogenic cocktails to improve vascular response in vivo and develop targeted engineered therapeutics for clinical uses.

A Hydrogel-Based Biomaterial for the Localized Delivery of Biologics

What problem does the invention solve? Many disease states suffer from insufficient tissue growth, healing, remodeling, and regeneration. Providing biological cues for advancing tissue function aids in recovery. These biologics, such as proteins, peptides, and growth factors, can be locally delivered in a controlled-release manner to impact specific regions of tissue and avoid degradation and unwanted side effects as often found with systemic (non-local) delivery.

A commonality amongst heart disease states and correlating regenerative medicine approaches lies in the need for stimulation of blood vessel development for tissue perfusion and ventricular remodeling, thus introducing a large overarching need within the field. Localized delivery of biologics, including angiogenic growth factors, showed the stimulation of vascular network formation, vessel development, and tissue perfusion.

Engineered cardiac tissues, a promising and highly researched regenerative approach, are currently challenged by limitations to maximum tissue thickness in vitro and in vivo. Without significant tissue vascularization soon after implantation, exceeding this maximum thickness results in a dead core at the center of the tissue. This minimal allowed thickness currently plagues the whole of the tissue engineering field, attenuating the potential for maximum therapeutic benefit. This motivated large volumes of research into methods of promoting or including vascularization of the tissue.

Mechanical testing evaluated the capability of a surgeon's injection control. Thin-film fabrication included molded handles for easy maneuverability and implant placement. The potential thinness of the implant and its transparency presents their own advantage in its novelty in the field and its ability to combine with other therapeutic interventions. The versatility of a single known and well-defined composition for application to such an extensive range of repair and regeneration space is predictive of user comfort with what would constitute a single, well-researched, and understood compound on the market.

State of the Art.

Persons having ordinary skill in the tissue engineering art often use stress fields resulting from tissue compaction in isometrically confined tissues as a surrogate to induce cell alignment. While often effective at inducing alignment, the available methods necessitate either tissue fenestrations (reducing the efficacy and efficiency of tissues with function related to mechanics and structure) or prescribe high-aspect-ratio tissues with limited utility as replacement tissue patches. This approach does not replicate the mechanical material anisotropy found in these native tissues and extracellular matrix (ECM), which is often a defining feature of these tissues and materials and may be necessary for cell and tissue development.

The soft tissue engineering community used a wide variety of natural and synthetic polymer hydrogel materials as accessible scaffold materials, permitting high customization for individual uses, as reviewed by Jafari et al., J. Biomed. Mater. Res. B Appl. Biomater. 105, 431 (2017). Tissue engineers can select from a vast library of hydrogel scaffolds defined by molecular composition and organization. Tissue engineers can therefore choose a composition best suited to their cell and tissue type of interest in terms of cell adhesion site availability and density, mechanical stiffness and strength, remodeling and degradation rates, cleavage sites, and many other parameters for tissue development. These systems cannot provide internal structural and organizational cues to resident cells.

Polymer microfibers embedded in a bulk hydrogel provide precise structural and mechanical cues to cells seeded in engineered tissues, offering tissue engineers another dimension of control in designing tissues for therapy and research. Several strategies for emulating extracellular matrix structural and mechanical cues in 3D engineered tissues in an array of shapes were used in the tissue engineering art, including aligned and unorganized nanofiber mats, aligned pores through directional freezing, spheretemplated and rod-templated scaffolds, and 3D printed scaffolds. All these strategies have effected significant changes on cell phenotype and function, demonstrating their value to the field and the importance of these mechanical and structural signaling cues. All these strategies require compromise in terms of thickness limitations, ease of cell infiltration, and precise control over the scaffold pattern or morphology. Aligned and unorganized nanofiber mats feature high surface areas and fiber densities, but the high fiber density can make cell infiltration challenging, especially in thicker mats. The fabrication of complex, well-defined patterns remains a challenge. Directional freezing can create uniform, anisotropic pore arrays in various natural and synthetic scaffold materials. Still, directional controlled rate freezing has constraints, such as singular freezing direction, which limit the morphologies that can be created. 3D printed scaffolds offer high reproducibility and broad design space, but compromises must be made on either resolution or scaffold polymer, often excluding natural polymer scaffolds.

Definitions

For convenience, the meaning of some terms and phrases used in the specification, examples, and appended claims, are listed below. Unless stated otherwise or implicit from context, these terms and phrases shall have the meanings below. These definitions aid in describing particular embodiments but are not intended to limit the claimed invention. Unless otherwise defined, all technical and scientific terms have the same meaning as commonly understood by a person having ordinary skill in the art to which this invention belongs. A term's meaning provided in this specification shall prevail if any apparent discrepancy arises between the meaning of a definition provided in this specification and the term's use in the tissue engineering art.

About has the plain meaning of approximately. The term about encompasses the measurement errors inherently associated with the relevant testing. When used with percentages, about means ±1%. About or approximately when referring to a value or parameter means to be within a range of normal tolerance in the art, e.g., within two standard deviations of the mean. A description referring to about X describes X.

Angiogenesis has the biomedical art-recognized meaning of the development of new blood vessels.

Cardiac fibroblasts have the biomedical art-recognized meaning of cells that produce connective tissue. Unlike the connective tissue of bone and tendon, which is organized into regular patterns of collagen, heart ECM is dense, irregular, and composed of collagens, proteoglycans, and glycoproteins.

Composite scaffolds are scaffolds made up of more than one constituent, often one organic material and another inorganic material that often have different physical forms in the combined scaffold, such as a fiber and a hydrogel.

Cytokine has the biomedical art-recognized meaning of a small protein important in cell signaling. Cytokines are peptides and do not cross the lipid bilayer of cells to enter the cytoplasm. As immunomodulating agents, cytokines can be involved in autocrine, paracrine, and endocrine signaling.

Design of Experiments (DOE) is a branch of applied statistics that deals with planning, conducting, analyzing, and interpreting controlled tests to evaluate the factors that control the value of a parameter or group of parameters. DOE helps plan which groups to test empirically to acquire data covering the experimental design space using fractional factorial design. Our approach used triplicate measurements from independent biological samples for each metric and each group of factors tested. Low and high concentrations of each factor are used in a 2-level fractional factorial design. Upon gathering all data from analyses of the new vessels in the gels, all metrics of vascularization are inputs into the DOE analysis. Statistically significant effects are determined with a p-value <0.05.

Growth factor has the biomedical art-recognized meaning of a substance, such as a secreted protein or a hormone, which is required to stimulate cell proliferation, migration, morphogenesis, wound healing, and occasionally cellular differentiation.

hiPSC-CMs have the biomedical art-recognized meaning of human-induced pluripotent stem cell-derived cardiomyocytes.

Human-induced pluripotent stem cells or hiPSC are a type of pluripotent stem cell that can be generated from adult cells. Human-induced pluripotent stem cells are a renewable source of human cells.

Matrigel plug assay has the biomedical art-recognized meaning of a method for the in vivo evaluation of proangiogenic and anti-angiogenic molecules. Matrigel is a laminin-rich reconstituted matrix, an extract of the Engelbreth-Holm-Swarm (EHS) tumor composed of basement membrane components. In the Matrigel plug assay, an angiogenic stimulus (usually recombinant growth factors or stem cells) is introduced into cold liquid Matrigel. After subcutaneous injection in rodents, the Matrigel solidifies at body temperature and enables the recruitment of a new microvascular network. The later immunohistochemistry (IHC) staining with the endothelial cell marker indicates the newly formed capillaries in the sectioned gel plugs. The Matrigel plug assay allows the simultaneous, quantitative evaluation of the newly-formed endothelium and of non-endothelial/inflammatory components of the cellular infiltrate in the Matrigel implant and the expression of genes involved in the modulation of the angiogenesis process.

Tissue engineering is the use of a combination of cells, engineering, and materials methods, and suitable biochemical and physicochemical factors to improve, mimic, or replace biological tissues. Tissue engineering involves using a tissue scaffold to form new viable tissue for a biological or medical purpose. The phrase tissue engineering is often interchangeably used with regenerative medicine.

Type I collagen is the most abundant collagen in the human body. It forms large, eosinophilic fibers known as collagen fibers. It is present in scar tissue, the end product when tissue heals by repair, and tendons, ligaments, the endomysium of myofibrils, the organic part of the bone, the dermis, the dentin, and organ capsules. The COL1A1 gene produces the pro-alpha1(1) chain. This chain combines with another pro-alpha1(I) chain and with a pro-alpha2(1) chain (produced by the COL1A2 gene) to make a molecule of type I procollagen. These triple-stranded, rope-like procollagen molecules are processed by enzymes outside the cell. After these molecules are processed, they arrange themselves into long, thin fibrils that cross-link in the spaces around cells. The cross-links result in the formation of firm mature type I collagen fibers.

The terms comprise and comprising should be interpreted as referring to elements, components, or steps in a non-exclusive manner, indicating that the referenced elements, components, or steps may be present, used, or combined with other elements, components, or steps. The singular terms a, an, and the include plural referents unless context indicates otherwise. The abbreviation e.g. is used to indicate a non-limiting example and is synonymous with the term for example.

Unless otherwise defined, scientific and technical terms used with this application shall have the meanings commonly understood by persons having ordinary skill in the biomedical art. This invention is not limited to the methodology, protocols, reagents, etc., described herein and can vary.

The disclosure described herein does not concern a process for cloning humans, methods for modifying the germ line genetic identity of humans, uses of human embryos for industrial or commercial purposes, or procedures for changing the genetic identity of animals likely to cause them suffering with no substantial medical benefit to man or animal and animals resulting from such processes.

Materials & Methods

Growth factors/cytokines: VEGF, bFGF, Shh, Ang-1, TGF-β1, MMP-9, PDGF, IGF-1, EGF, MCP-1. All possible combinations are likely to improve vascular responses. Thirty-two groups of gel containing growth factors at high (2 μg) and low (0.5 μg) doses were delivered and empirically evaluated in rat models.

Qualitative evaluation of hemoglobin content. Matrigel and biomaterial implants were imaged upon explant and rated on a scale from 0 (clear) to 3 (dark red) to assess hemoglobin saturation after seven days in vivo. Scale 0. Clear, lacks cells. Scale 1. Pink, little presence of cells. Scale 2. Pink/brown; moderate color saturation, some visible vessels. Scale 3. Red, highly saturated, with a large presence of cells, large vessels visible.

Evaluation by immunohistochemistry. Explanted gels were fixed by 4% paraformaldehyde and embedded in frozen blocks for sectioning and immunohistochemical analyses. Antibodies against human CD31, pan-CD31, RECA, von Willebrand factor, and VE-cadherin identify endothelial cells; αSMA identifies vascular smooth muscle cell-coated vessels (also by morphology), vimentin identifies stromal cells like fibroblasts; TER119 and autofluorescence of red blood cells identify blood-perfused vessels; and CD68, CD80, CD86, CD163, and CD206 identify macrophages and their subtypes. Secondary antibodies conjugated to Alexa fluorophores enable fluorescence imaging by confocal microscopy for widefield fluorescence slide scanning. Image analyses by unbiased imaging processing tools in MATLAB and Image J (Fiji) provide quantitative and semi-quantitative outputs.

Perfusion of vascular labels. Before sacrifice, intravenous injection of fluorescently labeled or biotinylated lectins was used to track perfused vessels in explants by fluorescence imaging of frozen sections from explants.

Vascular metrics: Multiple metrics were used to assess the quantity, dimensions, and morphology of new vessels in the gel implants. Metrics included hemoglobin content vessel lumen density, lumen diameter, vascular area per total area (fraction or percent), and perfused vessel density and area.

The following EXAMPLES are provided to illustrate the invention and should not be considered to limit its scope.

Example 1

Figure 2:
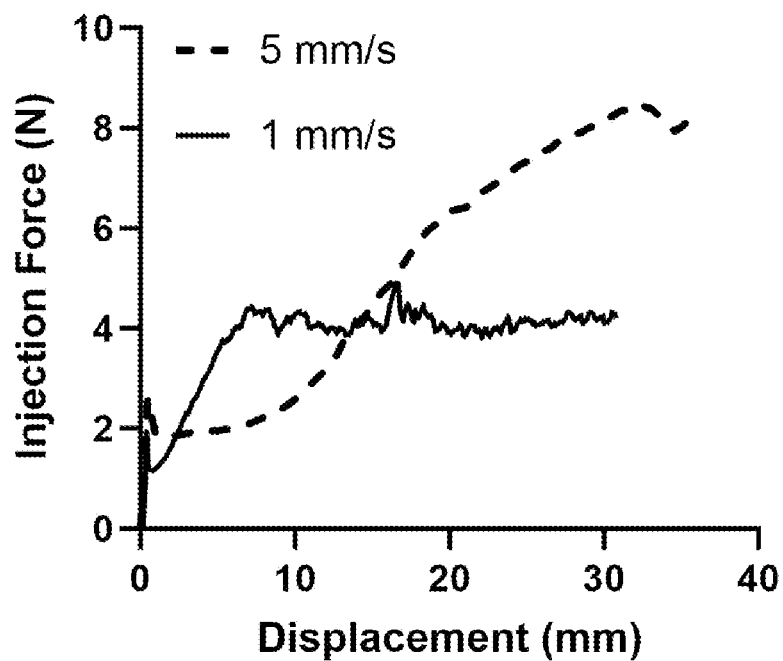
FIG. 2 is a line graph showing the results of two mechanical characterizations of the injectable gel where the slower speed requires less force to exude. The characterizations were performed using the methods of Vo et al., J. Med. Eng. (2016) and Peterson et al., Int. Pharm. Ind. (2016).
Figure 3A:
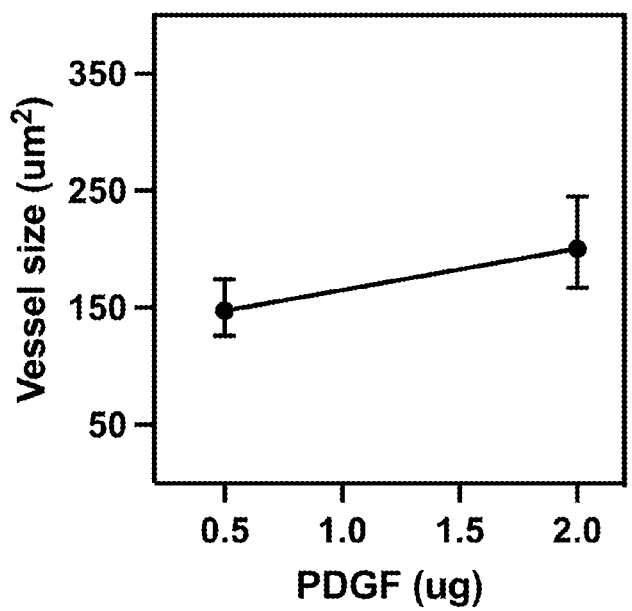
FIGS. 3A-3K are a set of line graphs showing the main effect and factor interaction plots for growth factors involved in statistically significant models for vessel size, CD31 area, total vascular area, and aSMA:CD31 area ratio. Assuming a linear relationship between factors, we can predict net positive and net negative effects on angiogenesis in vivo and ultimately determine highly potent growth factor cocktails promote vessel growth and perfusion in ischemic tissue.
Figure 3B:
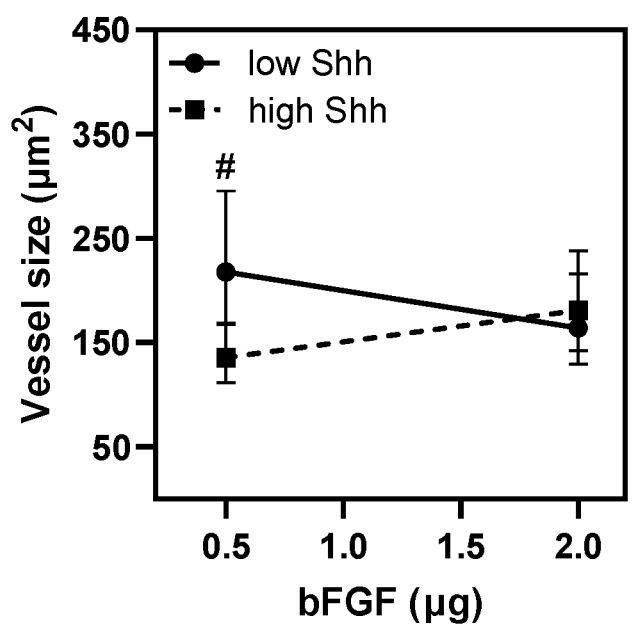
Figure 3C:
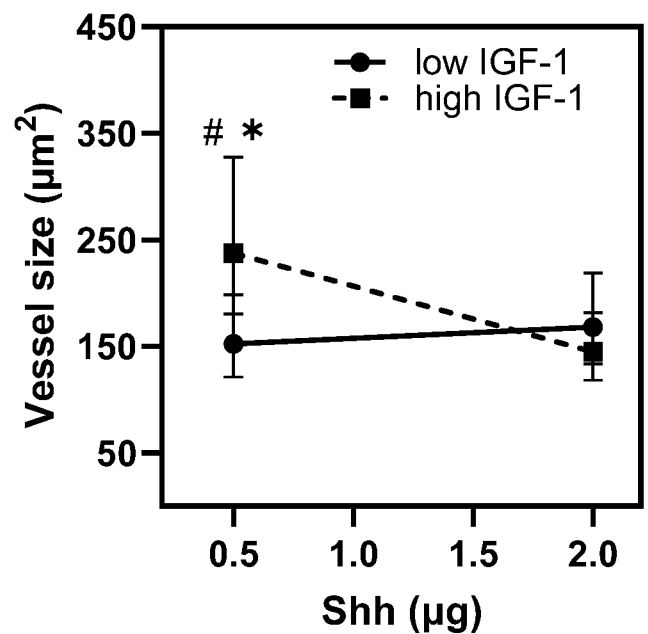
Figure 3D:
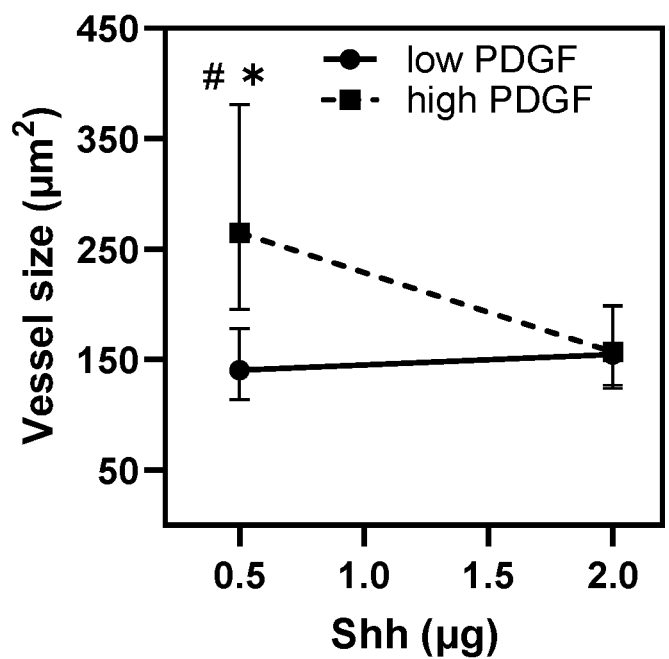
Figure 3E:
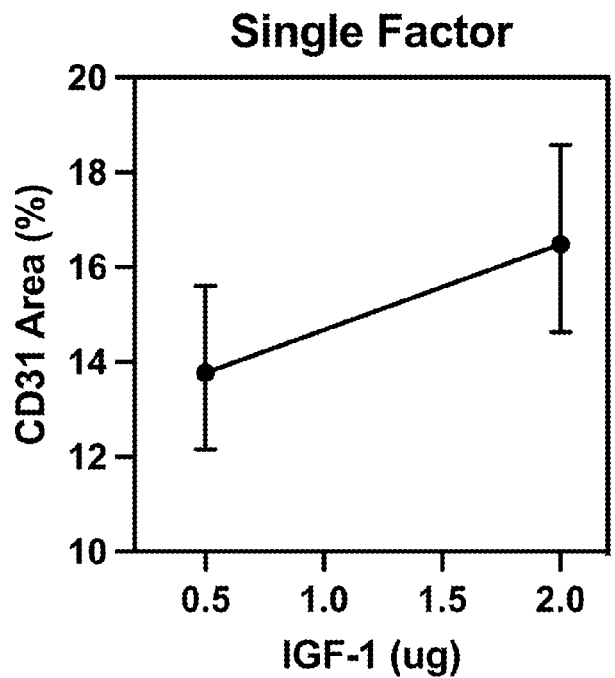
Figure 3F:
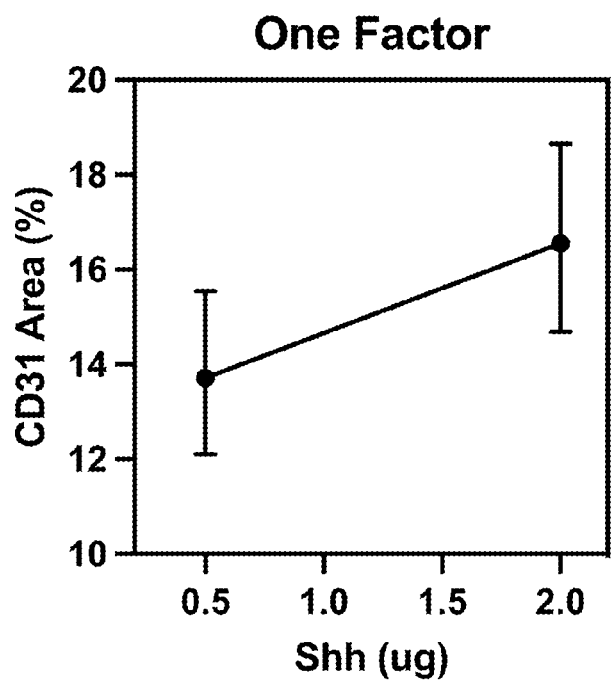
Figure 3G:
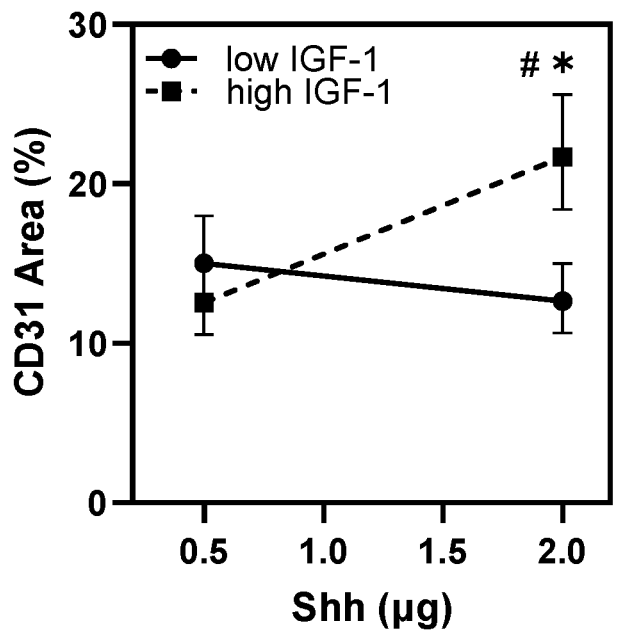
Figure 3H:
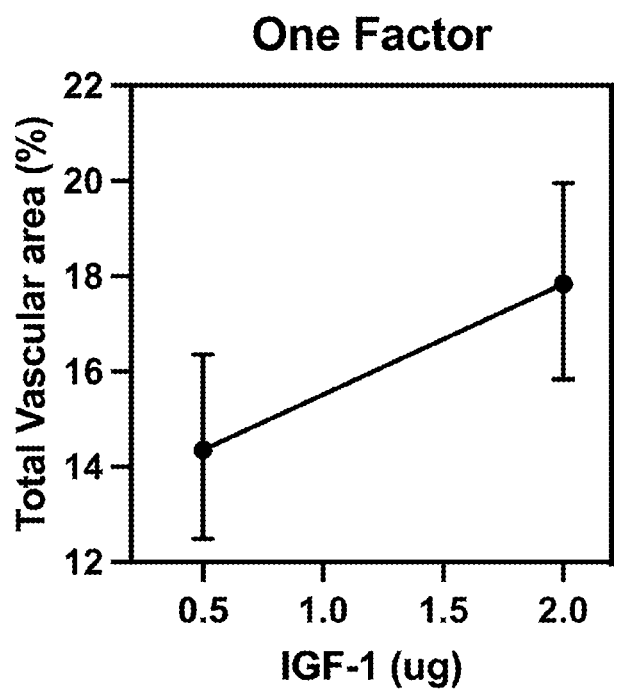
Figure 3I:
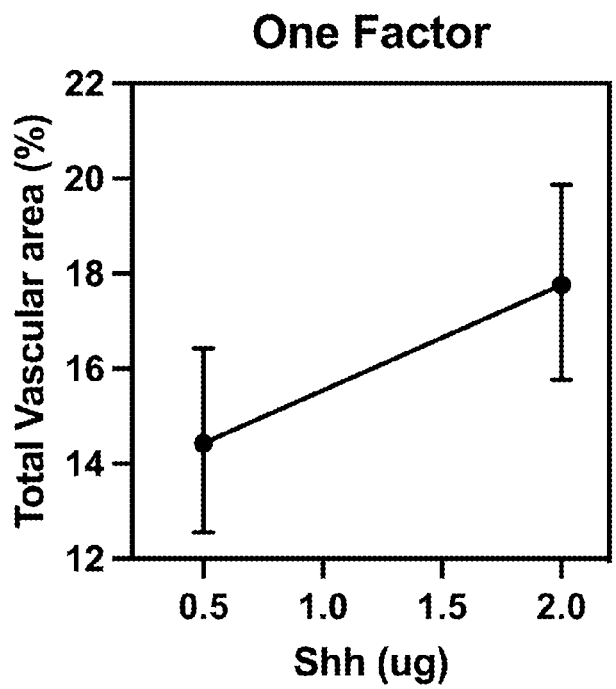
Figure 3J:
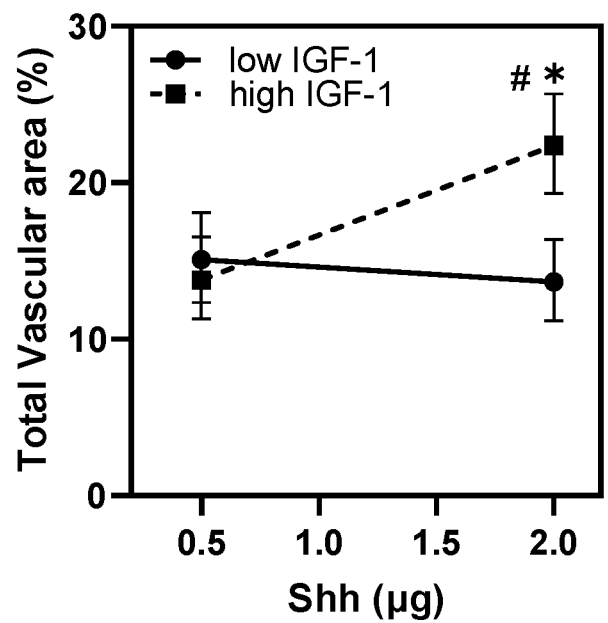
Figure 3K:
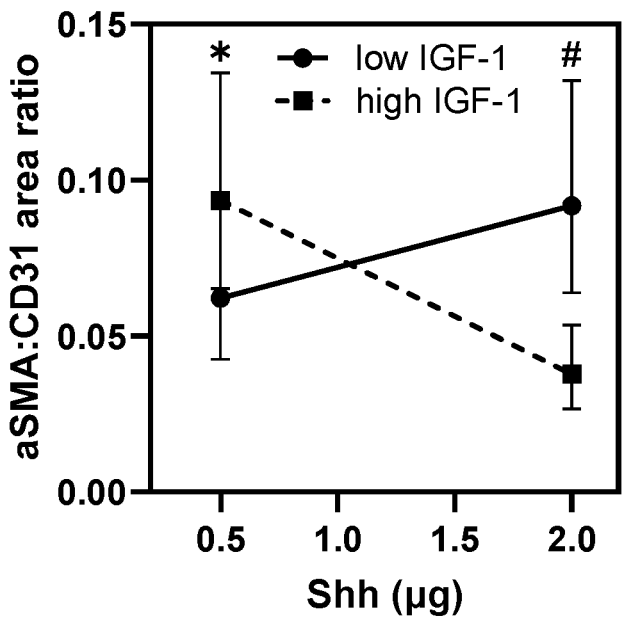
Figure 4:
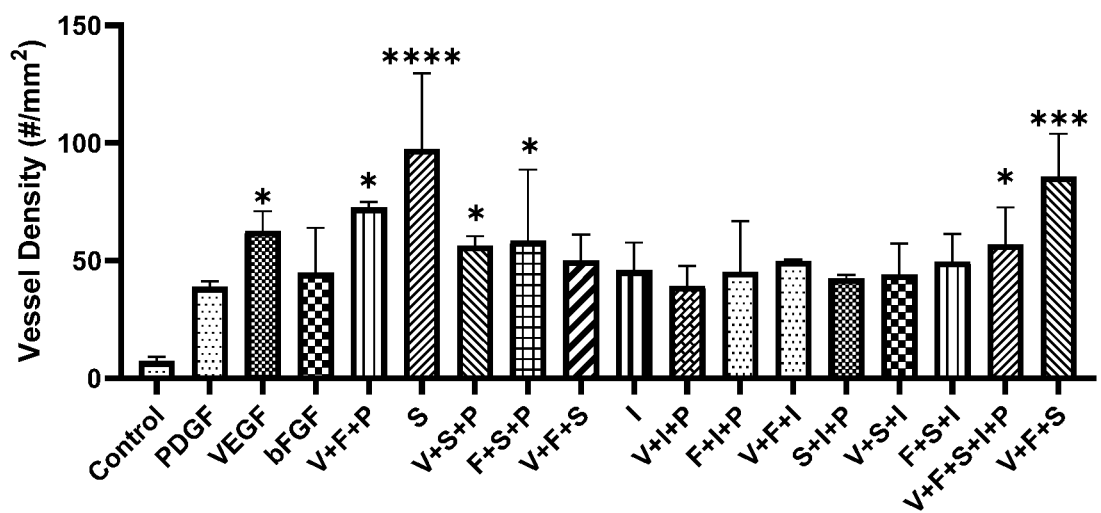
FIG. 4 is a bar graph of vessel density showing significantly greater densities achieved in growth factor-loaded gels than unloaded collagen-alginate hydrogels. Growth factors delivered in high doses are denoted on the x-axis: unloaded control (Control), VEGF (V), bFGF (F), Shh (S), IGF-1 (I), PDGF (P), and historical (VEGF, bFGF, Shh only).
Figure 5A:
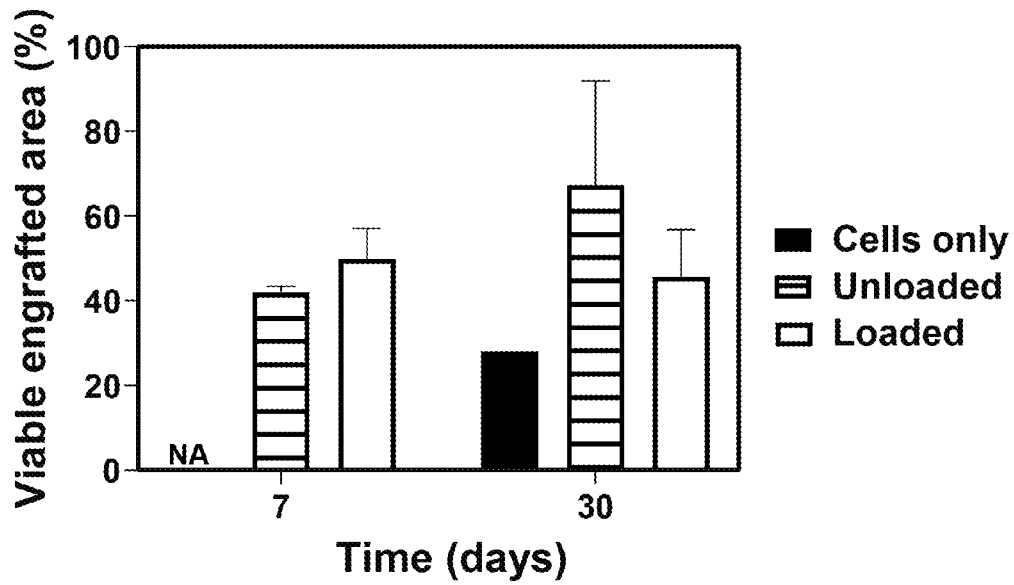
FIGS. 5A-5D are a set of graphs showing successful cardiac grafts and revascularization in a rat ischemia/reperfusion myocardial infarction model.
Figure 5B:
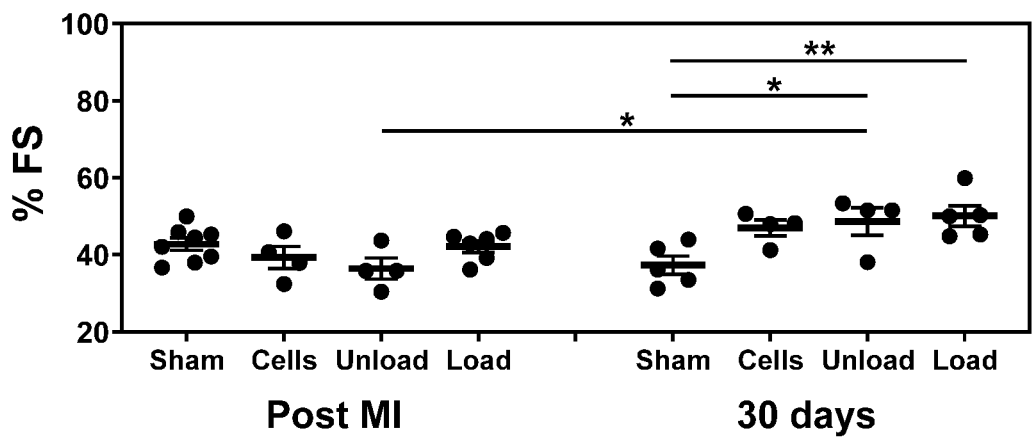
Figure 5C:
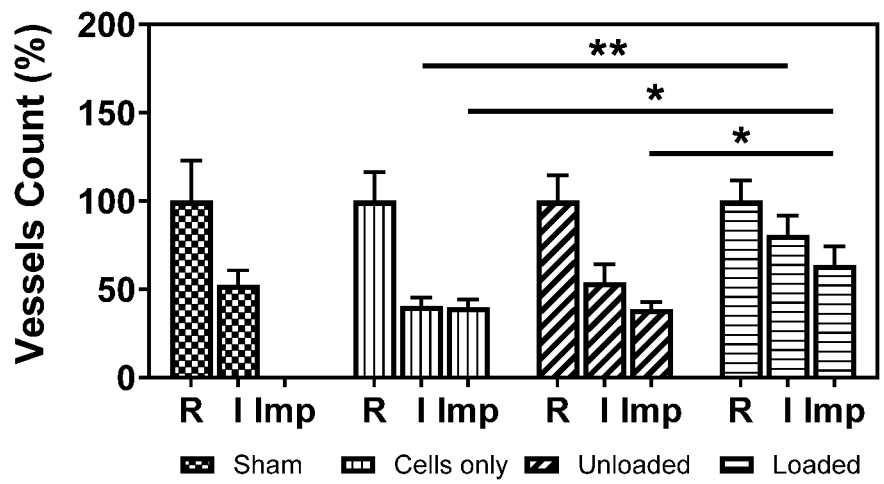
Figure 5D:
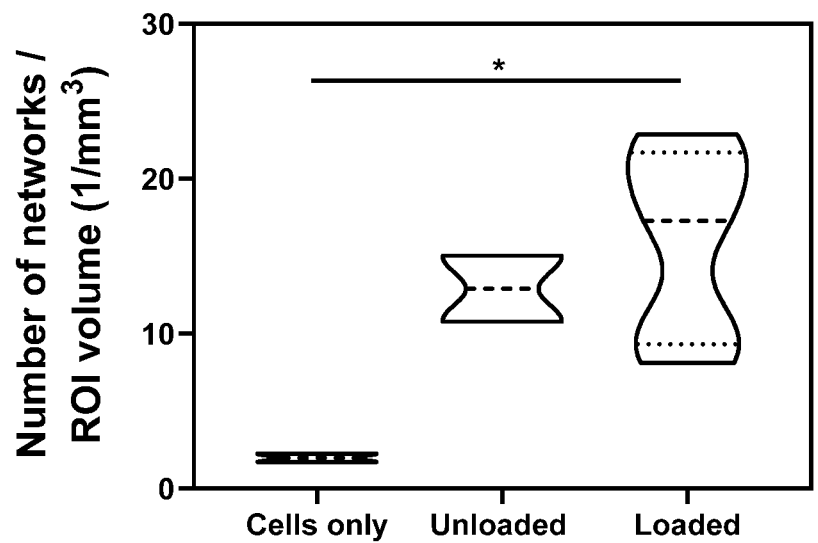
Figure 6:
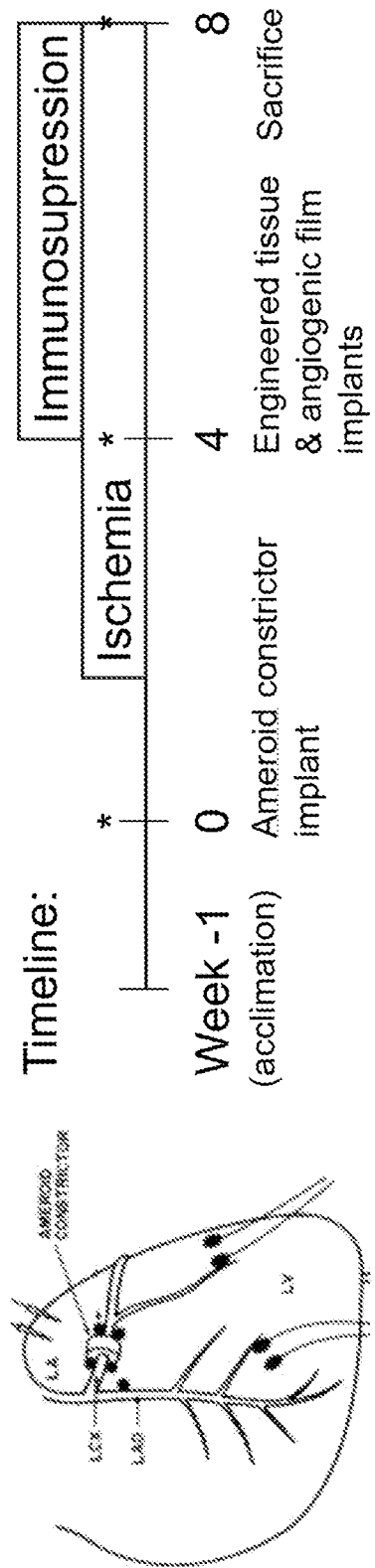
FIG. 6 shows that the surgical position of the ameroid constrictor (left) creates myocardial ischemia before implantation of the human-engineered myocardium with revascularization therapy. Functional assessments include ECG recording (weeks 0-8), longitudinal echocardiography, perfusion by microbead infusions, and optical mapping of implant excitation-contraction coupling activity.
Figure 7:
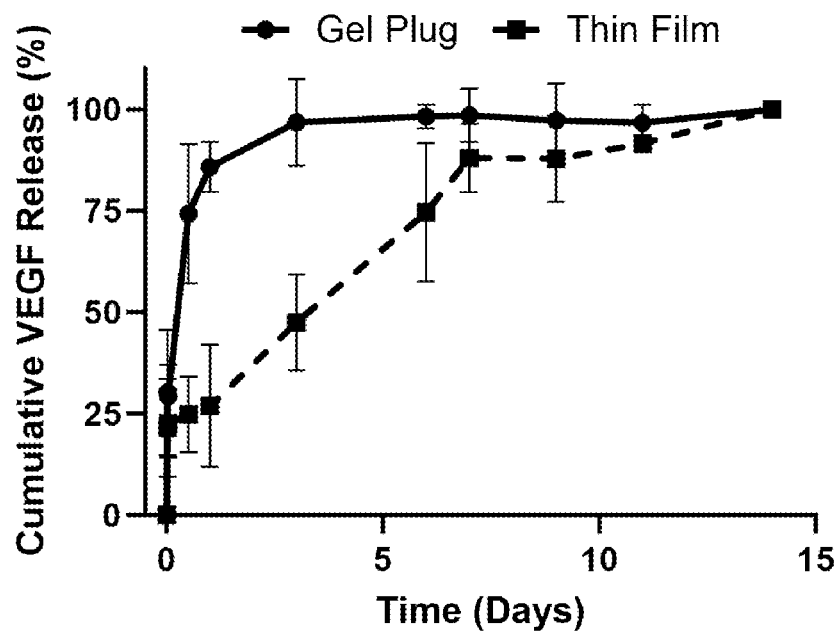
FIG. 7 shows release kinetics of two formulations of the biomaterial gel: an injectable gel plug and an implantable thin film. The release of VEGF from the film is slower and takes more time.
Figure 8:
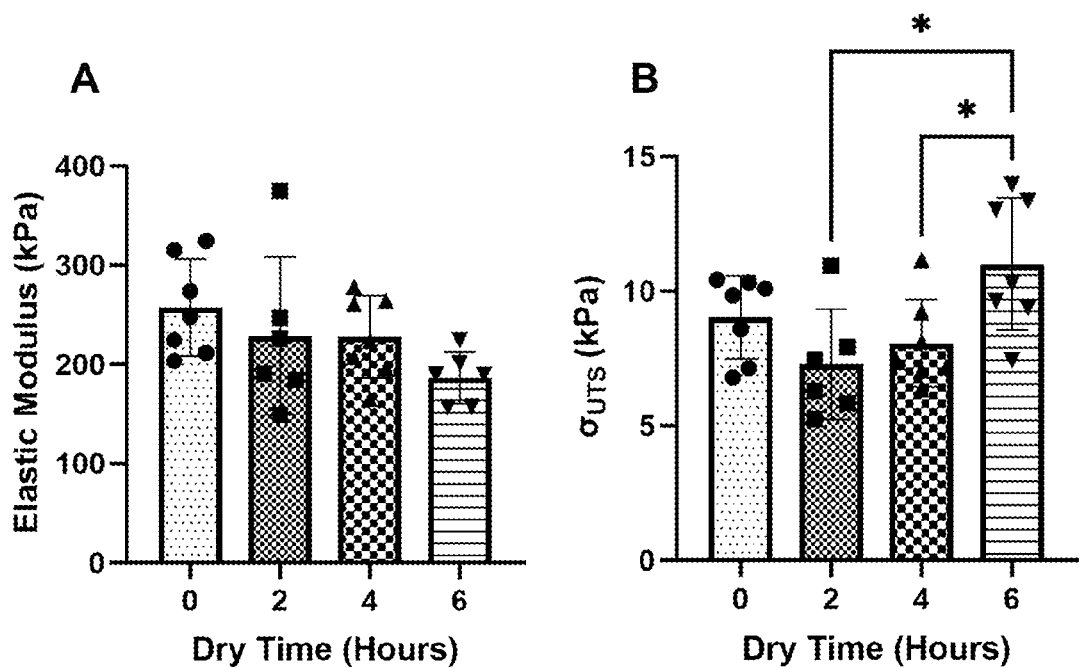
FIG. 8 shows that once the film is washed and prepared for implantation by removing excess fluid, the mechanical properties do not change due to drying over at least the first 4 hours.

Optimization of Heparinized Alginate-Based Hydrogels to Promote Vascularization in Cardiac Disease Hydro-gel injection in a pulmonary hypertensive rat model of the right ventricle. For fabrication methods, one begins with 1% heparin-alginate, then the addition of 1 mg/mL collagen, then 5 mg/mL $CaCO_3$. There was workable stiffness through day 5, with no discernable change in swelling capacity for injectable gel degradation and swelling behavior. The mechanical characterization of the injectable gel was performed using the methods of Vo et al., J. Med. Eng. (2016); and Peterson et al., Int Pharm Ind (2016) and an ISO 7886-1:2017 compliant machine. See the results in FIG. 2.

Co-implantation of a hydrogel thin-film in a post-myocardial infarction rat model. For fabrication methods, one begins with 2% heparin-alginate, adds 3 mg/mL collagen, then a 0.15 M $CaCl_2$ bath. For the thin-film degradation and swelling behavior, the gel was intact through day 7. There was minimal change in mass before failure. The mechanical characterization of the thin-film was performed using tensile testing in an Instron mechanical testing frame to measure elastic modulus and ultimate tensile strengths of 243 kPa and 9 kPa, respectively.

Alginate-based proangiogenic factor delivery. Stimulation of blood vessel development was produced via localized proangiogenic growth factors. Heparin functionalization improved factor binding and retention.

Conclusion. Heparinized-alginate and collagen hydrogels demonstrate tunable degradation and mechanical behavior, facilitating use in several delivery modes and cardiac diseases.

Example 2

Optimization of Heparinized Alginate-Based Hydrogels to Promote Vascularization in Cardiac Disease Many cardiovascular regenerative medicine approaches rely on blood vessel development for tissue perfusion and ventricular remodeling. Angiogenic growth factors and cytokines have demonstrated the ability to initiate angiogenesis and vascular network formation in cardiac tissue, with localization shown to be more effective than systemic delivery. See de Souza Reboucas et al., Arq. Bras. Cardiol., 271-275 (2016); Taimeh et al., Nature Rev. Cardiol., 519-530 (2013); and Gogiraju et al., Front. Cardiovasc. Med. (2019). These uses of proangiogenic factors have created the need for a similarly versatile delivery system. Alginate, with its high biocompatibility and tunable degradation, sets a good foundation for a hydrogel-based delivery. Heparinization of the alginate further improves factor binding and retention. Munarin et al., J. Biomed. Mater. Res. A (2021). Adding collagen both increases biointegration and allows greater tuning. Modulating these components across a range of concentrations and cross-linking methods allows for user-specific optimization of the system. In this EXAMPLE, injectable and implantable thin-film uses are developed and characterized.

Fabrication methods. Heparinized-alginate and collagen concentrations and subsequent cross-linking methods were optimized for two distinct delivery mechanisms. A surgically handleable thin-film containing 2% w/v heparin-alginate and 3 mg/mL collagen cross-linked in a bath of 0.15 M $CaCl_2$ was developed for co-implantation with an engineered tissue on the epicardial surface in a model of myocardial infarction. An injectable hydrogel containing 1% w/v heparin-alginate and 1 mg/mL collagen cross-linked using mixed-in 5 mg/mL $CaCO_3$ was developed for injection into the right ventricle wall of a pulmonary hypertension model. Each delivery use accommodated varying volumes of growth factors and cytokines with a sustained release for more than seven days. Degradation and swelling were evaluated using wet and dry sample weights. Mechanical testing was used to evaluate the forces required for extrusion of the injection and the tensile properties of the implantable thin-film.

Conclusions. The injectable and implantable formulations degraded in five and seven days, respectively, demonstrating the ability to modulate degradation rate based on the application-specific requirements. Evaluation of the break loose and peak forces during extrusion of the injectable formulation places the injectable within normal anthropometric ranges for injection depression and control for more than three hours following gelation. Vo A et al., J. Med. Eng. (2016). The lack of significant differences between the break-loose and dynamic glide forces suggests minimal patient pain and tissue trauma. Vo A et al., J. Med. Eng. (2016). Similarly, the high stiffness shown by the thin-film maintains handleability for more than six hours when stored in a humidity chamber. The successful application of the biomaterial to disparate delivery mechanisms and disease states demonstrates the versatile regenerative capabilities of the hydrogel design. Factor-specific release kinetics are being determined and in vivo assessments remain ongoing for specific uses, such as in the ischemic heart.

Localization of bioactive molecules was more effective than system delivery. Alginate, with its high biocompatibility and biodegradation, represents a promising hydrogel material for factor delivery. In this EXAMPLE, alginate, covalently coupled to heparin, is used to improve factor binding and retention to lengthen vascular-promoting factors' release time. For greater tuning and biointegration, collagen and the heparin-alginate mix were optimized for implantable and injectable delivery mechanisms. In vitro testing using human-induced pluripotent stem cell-derived endothelial cells (hiPSC-ECs) showed cell viability and primitive network formation. A surgically handled hydrogel film containing 2% w/v heparin-alginate and 3 mg/mL collagen cross-linked with 0.15 M $CaCl_2$ was developed for co-implantation with an engineered tissue in a model of myocardial infarction.

An injectable hydrogel containing 1% w/v heparin-alginate and 1 mg/mL collagen cross-linked using 5 mg/mL $CaCO_3$ was developed for injection in a pulmonary hypertension model of the right ventricle. The film and injectable formulations sustained growth factor and cytokine release for more than seven days. In vivo subcutaneous injection evaluation demonstrated notable vascularization within four days, with host-vessel penetration into the delivered biomaterial. The successful application of the biomaterial to disparate delivery models and disease states demonstrates the versatile regenerative capabilities of the hydrogel design.

Example 3

Identifying Potent Combinations of Angiogenic Factors to Stimulate Angiogenesis In Vivo The problem was: Which combinations of angiogenic factors should be delivered in engineered cardiac tissues to pattern vessel formation and support the function of implanted cardiomyocytes? The solution is: Identifying optimum combinations of growth factors and cytokines to target vascular cells and stimulate angiogenesis in vivo.

Combinations of growth factors and cytokines were found to collectively initiate angiogenesis in vitro and in vivo. The functionality of human engineered cardiac tissue and regenerative tissue therapies depend highly on the formation of vascular networks in vivo. Multiple growth factor cocktails containing vascular endothelial growth factor (VEGF), basic fibroblast growth factor (bFGF), and sonic hedgehog (SHH) have been incorporated in engineered scaffolds to elicit angiogenic responses in vivo and facilitate tissue integration. However, the interaction between VEGF, bFGF, Shh and other proangiogenic factors secreted during angiogenesis has not been well characterized.

Seven-day angiogenesis assays. In this EXAMPLE, the inventors investigated the effects often growth factors, cytokines and enzymes: VEGF, bFGF, SHH, platelet-derived growth factor (PDGF), insulin-like growth factor-I (IGF-1), matrix metalloproteinase-9 (MMP-9), heparin-binding epidermal growth factor (HB-EGF), angiopoietin-1 (ANG-I), monocyte chemoattractant protein-I (MCP-1), and transforming growth factor-beta 1 (TGF-β1) on endothelial and vascular cell plasticity (namely migration, vessel size and density) using a two-level, fractional factorial Design of Experiments (DoE) approach to quantitatively assess factor interactions. Matrigel plugs containing growth factors/cytokines at high (4 µg/mL) and low (1 µg/mL) concentrations were injected subcutaneously in wild-type rats to evaluate neovascularization over seven days. Plugs were assessed for hemoglobin content and histologically for host endothelial (CD31) and vascular smooth muscle (aSMA) cells in developing vessel networks, total vascular area (CD31+capillaries, $aSMA^+$ lumen) and vessel perfusion by red blood cells. The inventors integrated these metrics with response surface methodology (RSM) to determine optimum combinations of growth factors/cytokines that collectively induce angiogenesis in vivo.

Significant statistical models were generated for hemoglobin content, lumen density and cell recruitment ($CD31^+$ area). TABLE 1 shows the main effects and factor interactions in the hemoglobin model. The combination of bFGF and EGF has the most significant contribution at 10%.

TABLE 1

| Terms for Hemoglobin Content | p-value | % Contribution |
|---|---|---|
| Model | <0.0001 | |
| VEGF | 0.0123 | 3.5008 |
| bFGF | 0.2393 | 0.7489 |
| SHH | 0.0409 | 2.3042 |
| PDGF | 0.8943 | 0.00945 |
| IGF-1 | 0.0434 | 2.246 |
| MMP-9 | 0.0713 | 1.7815 |
| MCP-1 | 0.0056 | 4.333 |
| HB-EGF | 0.3103 | 0.5554 |
| Ang-1 | 0.0025 | 5.2248 |
| TGFβ1 | 0.0170 | 3.1708 |
| VEGF + bFGF | 0.0445 | 2.2233 |
| bFGF + MMP-9 | 0.0108 | 3.6360 |
| bFGF + EGF | <0.0001 | 10.1454 |
| SHH + PDGF | 0.0143 | 3.351 |
| SHH + IGF-1 | 0.0049 | 4.4664 |
| SHH + MMP-9 | 0.0360 | 2.4276 |
| PDGF + IGF-1 | <0.0001 | 9.9779 |

Significant factors and interactions for lumen development. For lumen diameter, fewer terms were significant. But see IGF-1 and the possible interaction between Shh and PDGF.

TABLE 2

| Terms for Lumen Density | % Contribution |
|---|---|
| VEGF | 0.104 |
| Shh | 5.77 |
| IGF-1 | 18.60 |
| Ang-1 | 1.83 |

TABLE 2-continued

| Terms for Lumen Density | % Contribution |
| --- | --- |
| VEGF + Ang-1 | 6.34 |
| Shh + PDGF | 13.92 |

TABLE 3

| Terms for Lumen Diameter | % Contribution |
| --- | --- |
| Shh | 0.041 |
| PDGF | 0.73 |
| IGF-1 | 17.62 |
| Shh + PDGF | 18.41 |

From these models, the inventors determined that five factors: VEGF, bFGF, Shh, IGF-1 and PDGF were highly potent by metrics of vessel density and vascular cell recruitment and warranted further study in a highly defined system to elucidate all main effects and two-factor interactions regulating vascular development. Evaluating the combinatorial effects of growth factors that achieve a robust vascular response will better inform the selection of growth factors and cytokines for tissue engineering and regenerative medicine applications.

Example 4

Identifying Potent Combinations of Angiogenic Factors to Engineer Cardiac Regenerative Therapies Previous studies have shown that combinations of growth factors and cytokines collectively initiate angiogenesis in vivo and facilitate vessel development, but the interaction between these factors is not well understood. In this EXAMPLE, the inventors further investigated the effects of five growth factors and cytokines previously determined to be most potent on endothelial and vascular cell plasticity in a two-level, fractional factorial Design of Experiments (DoE) approach to assess factor interactions quantitatively using the defined heparinized-alginate-co-collagen biomaterial.

Across all metrics measured for new vessel growth, the single factors that statistically increased vessel density, area, diameter, and perfusion to the greatest extent were IGF-1 and Shh. Also effective but to a lesser degree were bFGF, PDGF, and VEGF. The Design of Experiment approach enabled statistical analysis of 2-factor combinations that significantly improved vascular metrics. The most potent factors were (in rank order): IGF-1 plus Shh, Shh plus PDGF, IGF-1 plus PDGF, and Shh plus bFGF.

The aims of this EXAMPLE are to (1) elucidate the main effects, two-factor interactions, and three-factor interactions of five narrowed growth factors and cytokines on in vivo angiogenesis; and (2) determine which combinations of angiogenic factors produce a significant effect on vascular development when delivered in the previously described defined heparinized alginate and collagen hydrogel.

Immunohistochemical assessment of vascularization and perfusion in biomaterial implants. Representative sections from implants containing different formulations of growth factors. CD31 positive endothelial cells and αSMA positive vascular smooth muscle cells infiltrate implants and form vessel networks after seven days. Perfused vessels contain red blood cells. Lumen diameter and density quantified in Image.

Statistically significant models for Vessel size, and cell recruitment were determined. TABLE 4 lists the main effects and interactions for vessel size with PDGF being significant as a single factor and in combination with Shh. IGF-1 and Shh in combination was also highly significant.

TABLE 4

| Terms for Vessel Size | p-value | % Contribution |
| --- | --- | --- |
| Model | 0.0018 | |
| VEGF | 0.2303 | 2.09 |
| bFGF | 0.8957 | 0.024 |
| Shh | 0.1338 | 3.32 |
| IGF-1 | 0.2919 | 1.61 |
| PDGF | 0.0169 | 8.91 |
| VEGF + Shh | 0.0691 | 4.96 |
| VEGF + IGF-1 | 0.0638 | 5.17 |
| bFGF + Shh | 0.0255 | 7.70 |
| Shh + IGF-1 | 0.0241 | 7.87 |
| Shh + PDGF | 0.0233 | 7.97 |
| IGF-1 + PDGF | 0.0581 | 5.42 |

TABLE 5 shows main effects and interactions for CD31+ area, with the interaction between Shh and IGF-1 having the greatest contribution with 26.64%.

TABLE 5

| $CD31^+$ area | p-value | % Contribution |
| --- | --- | --- |
| Model | <0.0001 | |
| Shh | 0.0339 | 7.23 |
| IGF-1 | 0.0418 | 6.63 |
| Shh + IGF-1 | 0.0001 | 26.64 |

TABLE 6 shows main effects and interactions for aSMA:CD31+ area and similar to CD31+, the interaction between Shh+IGF-1 has the greatest contribution to the model.

TABLE 6

| aSMA:CD31 area | p-value | % Contribution |
| --- | --- | --- |
| Model | 0.0019 | |
| Shh | 0.1576 | 3.69 |
| IGF-1 | 0.1913 | 3.14 |
| Shh + IGF-1 | 0.0009 | 23.01 |

Conclusions. Multiple angiogenic factors and defined mixtures are potent modulators of vessel growth. Combinations of VEGF, bFGF, and Shh direct vessel growth and increase capillary density in engineered cardiac tissue. Munarin et al., Biomaterials, 251, 120033 (2020). In this EXAMPLE, vessel network formation depends on the formulation of growth factors in implants. Several potent combinations drive vascular response in vivo. Recent studies using the in vivo Matrigel plug and defined heparinized-alginate-co-collagen biomaterial plug assays show IGF-1, PDGF, Shh, bFGF, and VEGF all promote vessel formation individually and in specific combinations.

The single factors with the most significant positive effect on vessel growth in the Matrigel implants were first IGF-1 and second Shh. Both performed well in the defined heparinized-alginate-collagen biomaterial implants, increasing the $CD31^+$ endothelial cell area. PDGF alone in the defined biomaterial increased the lumen diameter of the vessels.

Example 5

Heart Regeneration in a Porcine Model of Chronic Myocardial Ischemia

Ischemic heart disease (IHD) due to atherosclerosis or heart attack reduces the contractile function of surviving cardiomyocytes (CMs) or the total number of cardiomyocytes by apoptosis. Patients permanently lose heart function, necessitating medical intervention, as most patients suffering from ischemic heart disease experience progression to heart failure with reduced ejection fraction. Drugs such as beta-blockers, ACE inhibitors, and diuretics are prescribed to support cardiac contractility. Patients who become refractory to maximal medical therapy over months or years have limited treatment options: mechanical circulatory support or transplant. The field of heart regeneration has been providing new cardiomyocytes derived from human-induced pluripotent stem cells (hiPSCs) to the injured heart for over a decade. These therapies show that heart function can stabilize or even improve in large animal preclinical models, despite the prevalence of arrhythmias until the electrical coupling is achieved at ~four weeks. See Liu et al., Nature Biotechnol, 36(7), 597-605 (2018); Romagnuolo et al., 12(5), 967-981 (2019).

Human clinical trials began in Europe and use hiPSC-derived cardiac progenitor cells or terminally differentiated cardiomyocytes in engineered tissues for heart regeneration. See Menasche et al., J. Am. Coll. Cardiol., 71(4), 429-438 (2018.) or NCT04396899. Heart regeneration strategies are advancing in patients with a background of ischemia and thus compromised blood flow due to vascular perfusion challenges. Therefore, improved vessel growth and development in the injured heart are urgently needed.

A persistent challenge is the nominal vascular integration of hiPSC-CMs with host myocardium, which has not been directly addressed but is required for restoration of myocardial perfusion and survival, growth, and maturation of cardiomyocytes for contractile function. A critical aspect of this integration is the blood supply to implanted muscle cells, and this requires a vascular bed to grow from the host, remodel to increase blood perfusion, and connect from the host into new vessels in the implants.

The general purpose of this EXAMPLE is to re-engineer contractility in the heart by using hiPSC-CMs in engineered cardiac tissue with a biomaterial co-therapy to deliver vasculogenic factors for a biomaterial co-therapy to deliver vasculogenic factors for revascularizing and regenerating myocardium of injured hearts. The specific purpose of this EXAMPLE is to demonstrate the feasibility of implanting engineered human myocardium with a co-vascular biomaterial therapy in a clinically-relevant chronic ischemia model in the pig. The rationale is that revascularization therapy addresses chronic ischemia by providing vascular growth cues to improve myocardial perfusion and perfusion of the implanted cardiomyocytes needed to remuscularize the ventricular wall. The myocardium requires capillaries for cardiomyocyte survival, maturation, and contractile function. Thus, this EXAMPLE provides a vascularization strategy with angiogenic proteins delivered locally with the engineered human myocardium in chronic ischemic tissue. An instructive implant with local angiogenic factors increases myocardial perfusion and enables hiPSC-CM engraftment and tissue vascularization.

Prior results using the rat ischemia/reperfusion myocardial infarction model (see EXAMPLES above) show that localized release of angiogenic factors significantly enhances host-derived vessel development and perfusion in the scar and engineered cardiac tissue. The ischemia/reperfusion (I/R) myocardial infarction (MI) model mimics a heart attack. The left anterior descending (LAD) coronary artery is occluded using a temporary suture for 30-90 minutes, which impacts the cardiac injury. A heart attack can also be surgically induced by permanently closing or ligating the LAD. However, the I/R injury model allows blood to reperfuse through the vessel, miming coronary angioplasty that patients receive in the catheterization lab when presenting to an emergency room (ER) with a heart attack. Further, reperfusion of blood causes notable additional injury to the tissue after an extended period of ischemia due to immune cell infiltration, so the I/R model captures the phenomenon of "reperfusion injury" for a more clinically relevant wound bed in the heart. Munarin et al., Biomaterials, 251, 120033 (2020).

The pig model of chronic ischemia recapitulates key features of patient ischemic heart disease (IHD) because there is a slow narrowing of the artery (over 10-14 days) after placement of the ameroid constrictor, rather than an acute blockage. This is a good model for demonstrating persistent or chronic ischemia, as the narrowing does not change. Rather, the heart must adjust to low blood flow over time, making this a good model to study engraftment of engineered tissue and vessel development when the native vessel remains partially to fully occluded.

Enhance perfusion in the ventricular myocardium and engineered tissue implant using hiPSC-cardiac tissue with localized angiogenic therapy. The epicardial implant with revascularization co-therapy should enhance vessel morphogenesis and perfusion of the ischemic region and implanted hiPSC-cardiac tissue in the ischemic pig heart. The inventors induce chronic myocardial ischemia with surgical implantation of an ameroid constrictor and inject microbeads at 0, 4 and 8 weeks later to track the ischemic territory and capture functional changes by 2D echocardiography. Human engineered myocardium is implanted with an overlaid angiogenic biomaterial film. Four weeks after implant (at week 8), myocardial perfusion is assessed by injection of stable isotope-labeled microbeads. Immunohistochemistry is used to quantify vessel density in ischemic and remote heart regions and within the implant.

Remuscularize the ventricular wall to unload the host myocardium and promote systolic function. Co-delivery of hiPSC-CMs in the engineered tissue and the biomaterials-based revascularization therapy should enable contractile function in hearts. In pigs receiving dual remuscularization-revascularization therapy, the inventors use 2D echocardiography to assess whole heart function with fractional shortening and regional ventricular wall mechanics by strain analysis.

This EXAMPLE demonstrates the efficacy of implanting engineered human myocardium co-delivered with an angiogenic biomaterial film in a large animal model of chronic ischemic heart disease. Implants delivering hiPSC-CMs with angiogenic biomaterials in engineered tissues in a rat ischemia/reperfusion myocardial infarction model show efficacy in establishing cardiomyocyte engraftment and promoting new vessel growth and perfusion in both the ischemic region and implant itself. See Munarin et al., Biomaterials, 251, 120033 (2020).

This EXAMPLE is technically innovative. First, the inventors separated the production of the engineered cellular tissue from the protein-releasing biomaterial by creating an implantable thin film that can be surgically sutured over the engineered tissue. The angiogenic proteins are released locally from above the tissue, promoting vessel penetration into the tissue and not prematurely released during in vitro tissue culture, thus maximizing protein delivery in vivo. Second, the inventors use the pig model of chronic myocardial ischemia, where the surgical placement of an ameroid constrictor causes slow occlusion (over ~two weeks) of the coronary artery and produces ischemic disease very similar to that of patients without the dense scar deposition observed in rodent myocardial infarction models. The therapeutic implants occur four weeks after constrictor placement. The inventors quantify perfusion and heart function after another four weeks to assess the durable hiPSC-CM engraftment and persistence of new vessels. The conceptual innovation of this EXAMPLE lies in its localized vascularization approach that is integrated with the delivery of one billion dense hiPSC-CMs in a single mature, compact engineered tissue. No group has attempted a dual revascularization-remuscularization system in a clinically relevant large animal model of heart disease, and the potential benefits of implanting a single mass of hiPSC-CMs on perfusion, contractility, and arrhythmia reduction could be transformative.

The three phases of the EXAMPLE are (1) hiPSC-CM generation and tissue engineering, (2) pig surgeries for establishing ischemia and implanting the therapeutic tissue, and (3) terminal data collection and analyses.

Derivation of high purity hiPSC-CMs. The inventors use chemically defined culture conditions for hiPSCs (WTC GCaMP6f hiPSC line, Gladstone Institutes) and directed differentiation into ventricular cardiomyocytes by a well-established small molecule protocol for activating and inhibiting the Wnt signaling pathway to drive mesoderm and cardiogenesis. See Lian et al., Nature Protocols, 8(1), 162-75 (2013) and Burridge et al., Natures Methods, 11(8), 855-60 (2014). The inventors use metabolic-based purification and maturation using lactate-containing culture media, which yields cardiomyocyte purities >80% by flow cytometry analysis of cTnT. Further, the inventors induce proliferation of terminally differentiated hiPSC-CMs using Wnt activation and amplified cell counts by at least 50% with each low-density passage. Buikema et al., 27(1), 50-63 e5 (2020).

Formation of human-engineered myocardium and an angiogenic film. The inventors established methods to form engineered human myocardium in customized molds using natural collagen matrix protein as a bulk hydrogel that encapsulates hiPSC-CMs mixed with cardiac fibroblasts for enhanced tissue compaction, syncytium formation, and uniform contraction. See Munarin et al., 23(5), 311-321 (2017); Rupert, Irofuala, & Coulombe, PLoS One, 15(3), e0230001 (2020); and Rupert et al., Stem Cells International, 2020, U.S. Pat. No. 9,363,809 (2020). This simple system enables one to customize the size and geometry of the tissues for any application, and the inventors typically use 1.2×1.2 cm tissues with ~0.5 mm thickness for an implant on rat hearts.

The inventors developed an alginate-collagen film with enhanced retention of growth factors using heparin-bound alginate for an implant over the engineered cardiac tissue.

Chronic myocardial ischemia in a swine model. A small left thoracotomy is performed through the third or fourth intercostal space, the pericardium is opened, and a titanium ameroid constrictor of 1.75 mm in internal diameter is placed around the proximal left circumflex (LCX) coronary artery. See Harada et al., J. Clin. Invest., 94(2), 623-630 (1994); Voisine et al., Surgery, 136(2), 407-415 (2004); and Ruel et al., Circulation. 108 Suppl 1, 11335-40 (2003). Slow swelling of the constrictor reduces blood flow over 10-14 days, causing the slow onset of ischemia. Perfusion analysis by microbead injection identifies the ischemic territory downstream of the LCX (with left atrial injection at the time of therapeutic intervention surgery) and collateral development for improved perfusion with injection at terminal surgery. Terminal physiological assessments have shown constriction of the left circumflex artery by angiography (as expected) and a 20% increase in flow four weeks after VEGF infusion as measured by LCX-to-left anterior descending (LAD) coronary artery flow. See Voisine et al., Surgery, 136(2), 407-415 (2004).

This EXAMPLE addresses a critical need for developing new therapies to regenerate the native heart tissue in the setting of chronic ischemic heart disease. By using a highly translationally relevant swine model of chronic myocardial ischemia, the inventors aim to validate a dual revascularization-remuscularization approach by assessing myocardial and implant perfusion and whole heart function. These are integrated. Data collection addresses poignant questions in the field around vascular co-regeneration and electromechanical physiological response.

Enhance perfusion in the ventricular myocardium and engineered tissue implant using hiPSC-cardiac tissue with localized angiogenic therapy. Delivery of angiogenic growth factors VEGF or bFGF via solution injection in this chronic myocardial ischemia swine model has shown improved perfusion by microbead analyses. See Voisine et al., Surgery, 136(2), 407-415 (2004); Ruel et al., Circulation. 108 Suppl 1, 11335-40 (2003). New muscle was not established. Contractile function was not improved, motivating the transplantation of hiPSC-CMs into the heart to generate new cardiac muscle.

Injections of hESC-CMs into the left ventricle wall at several locations in swine (see Romagnuolo et al., Stem Cell Reports, 12(5), 967-981 (2019)) and macaque (see Liu et al., Nature Biotechnology, 36(7), 597-605 (2018)) ischemia/reperfusion myocardial infarction models have shown dire ventricular arrhythmias from the time of implant until four weeks post-implant despite large human cardiac cell engraftment, persistence and maturation/alignment of hiPSC-CMs over ≥four weeks, and some functional improvements in contractility.

There is an urgent need to consolidate all transplanted hiPSC-CMs into a single, matured engineered tissue implant on the epicardial surface to maintain engraftment and reduce arrhythmias. Ventricular tissues containing hiPSC-CMs over twenty-four days of differentiation that were purified and matured by lactate-based culturing methods and formed into tissues with 5% human cardiac fibroblasts become electrically quiescent. See Rupert, Irofuala, & Coulombe, PLoS One, 15(3), e0230001 (2020). The inventors demonstrated that co-transplantation of human-engineered myocardium with an alginate biomaterial releasing angiogenic growth factors improves the vascularization response in a rat ischemia/reperfusion myocardial infarction model.

HiPSC-CM differentiation, proliferation, purification, and maturation. HiPSC-CMs are differentiated as described above, proliferated by application of 2 μM CHIR99027 in low-density culture, and purified by metabolic selection using a DMEM-based medium with 4 mM lactate, with no glucose. Cardiomyocyte purity greater than 80%, as assessed by flow cytometry for cTnT, is used for tissue engineering. Maturation is accomplished by culture greater than twenty-four days and growth in a lactate-based medium, which shifts the metabolic profile of cardiomyocytes towards oxidative phosphorylation. Rupert, Irofuala, & Coulombe, PLoS One, 15(3), e0230001 (2020). HiPSC-CMs are frozen and stored to ensure adequate cell numbers and purities.

Human-engineered myocardium. One billion ($1\times10^9$) cardiomyocytes are mixed with 5% human primary ventricular cardiac fibroblasts (Lonza) and 1.8 mg/mL rat tail collagen type 1 and pipetted into molds (up to 7×8 cm). Culture for four to seven days allows tissue compaction and formation of uniform electrical syncytium and beating.

Tissues are cultured and then implanted. Fluorescent imaging of the genetically encoded GCaMP calcium indicator is used to quantify the spontaneous rate and electrically paced responses to increases in the frequency of the engineered tissues before implantation.

Angiogenic biomaterial film. Heparin-conjugated alginate (2% w/v) mixed with 3 mg/mL collagen 1 and the protein factors to be delivered by the biomaterial is pipetted into a porous nylon mesh frame with a width of 0.5-1 cm and open central area up to 6×8 cm, cross-linked in the presence of 0.15 mM $CaCl_2$ until gelled, and maintained hydrated under sterile conditions in minimal volume to reduce early protein release from the biomaterial. This film is rinsed to remove excess calcium immediately before implantation in a solution of sterile phosphate-buffered saline. VEGF and bFGF are two potent angiogenic factors used in the rat ischemia/reperfusion myocardial infarction model and prior studies in this swine model to enhance collateralization and perfusion. See Voisine et al., Surgery, 136(2), 407-415 (2004) and Ruel et al., Circulation, 108 Suppl 1, 11335-40 (2003). Experiments identified IGF-1 and Shh as potent vasculogenic factors. These two were used (800 µg total protein) for implants in the swine heart. The biomaterial film is laid on the engineered tissue and sutured in place.

Swine model. Yorkshire swine of either sex (Sinclair Research Inc., Colombia, MO, USA), weighing between 22 kg and 25 kg at the time of the initial procedure, are used. This EXAMPLE uses two pigs. The pigs receive an ameroid constrictor placement around the proximal LCX. Four weeks later, the dual revascularization-remuscularization therapeutic is implanted, and immunosuppression begun. Pigs are regularly monitored for ECG abnormalities and, four weeks later, sacrificed for physiological assessments and other terminal endpoints.

Two-dimensional echocardiography. Functional analysis of cardiac contractility is assessed at zero, four, six, and eight weeks in sedated pigs using 2D echocardiography of the left ventricle (LV). ECG is simultaneously recorded. 2D video captured over at least five cardiac cycles.

Microbead infusions. Stable-isotope labeled microbeads are injected into the left atrium at zero, four, and eight weeks at the beginning of surgery using a different isotope at each timepoint. The beads become lodged in the microcirculation of perfused tissue, enabling the identification of regions perfused. Myocardial samples from the remote, ischemic, and implant areas are analyzed commercially at sacrifice. See Voisine et al., Surgery, 136(2), 407-415 (2004).

Therapeutic implant. Engineered myocardium is implanted at four weeks, positioned over the left ventricle's ischemic zone, and sutured in place. The angiogenic biomaterial film containing 400 µg, each, of IGF-1 and Shh is sutured over the top.

Tissue analyses and immunohistochemistry. Hearts are explanted, sliced in the transverse plane, and samples taken for microbead analyses. Slices are fixed for immunohistochemical analyses. Anatomical landmarks are used to section around the left ventricle for routine processing, embedding, and sectioning. Tissue sections are labeled for CD31 to identify endothelial cells, αSMA to identify vascular smooth muscle cells (with circular morphology around endothelial cells to indicate a stabilized vessel), cTnT to label cardiomyocytes, huKu80 to label human nuclei, and TER119 to identify red blood cells. Slides are scanned. Digital images are analyzed and quantified based on the myocardial region (remote, ischemic, or implant).

Before implantation, the human-engineered myocardium should have very low or negligible spontaneous beating rates, which reflects a quiescent ventricular state and stable resting membrane potential. From perfusion analyses, the inventors expect to find narrowing of the LCX and reduced perfusion at week 4 but increased perfusion of the ischemic zone due to collateral vessel formation at week 8 by microbead and immunohistological assessments in the treated pigs compared to historic controls. The perfusion of new vessels is to be identified by containing $TER119^+$ red blood cells. The inventors expect small vessel density (≤50 µm diameter lumens) due to angiogenesis in the tissue implant to be ≥50% of the remote myocardial vessel density, as shown in the rat studies.

The inventors have a history of generating large numbers of hiPSC-CMs and creating robust tissues, despite the increased size required for pig implants (7×8 cm, $1\times10^9$ hiPSC-CMs).

Remuscularize the left ventricle wall to unload the host myocardium and promote systolic function. Contractile deficits in the heart due to ischemia are driven by local impairment of excitation-contraction coupling at the cellular level and result in global reductions in cardiac output. Furthermore, cardiac remodeling as a compensatory mechanism to improve cardiac output causes the heart muscle to hypertrophy or the left ventricle chamber to dilate. Longitudinal imaging is used clinically to track heart function and is most often documented using 2D ultrasound to obtain echocardiographic images and videos. From these images, typical metrics quantified include left ventricle dimensions at end-systole and end-diastole and ejection fraction, which is calculated as the percent (%) of blood volume ejected. This is a three-dimensional metric (3D) estimated from two-dimensional images. Use of left ventricle wall motion or strain (defined as the change in length compared to initial length) is used in patients to examine regional deficiencies, such as in myocardial infarction, where contractile wall thickening may be diminished in the region of the myocardial infarction. These analyses of wall strain provide regional contractility comparisons on a smaller scale than the whole tissue, approaching local tissue mechanics on a smaller scale. The inventors have the computational tools to correlate regional myocardial perfusion with regional wall strain to evaluate the impact of the dual revascularization-remuscularization therapy in the pig chronic ischemia model.

All methods for establishing infarct and implant are described above for the pigs used in this EXAMPLE with the addition of analyses for functional contractility of the left ventricle.

Whole left ventricle function and regional wall strain from 2D echocardiographic images. Collection of 2D echocardiographic images as described above enable the capture of transverse (short axis) images at the mid-papillary level at zero, four, six, and eight weeks. One can analyze videos offline for fractional shortening of the left ventricle from peak diastole to peak systole. Wall strain is quantified from videos from peak diastole to peak systole in six anatomical regions around the ventricle and in the endocardial, mid-wall, epicardial, and implant areas (visualized as nearly concentric circles to partition the left ventricle wall). Both radial and circumferential strain are analyzed from these planar views (using circular coordinates centered at the lumen centroid). Regional mechanics are correlated with regional perfusion from microbead analysis.

There should be a decline in fractional shortening from zero to four weeks and regional deficits in wall strain in the ischemic territory. There should be an observable improved strain at eight weeks in the ischemic zone and the location of the implant.

The inventors can collect 2D echocardiographic videos to analyze fractional shortening and wall strain without problems. However, suppose limits exist to the software capabilities for strain analysis. In that case, the inventors can use custom algorithms in MATLAB to extract fractional shortening, fractional area change of the left ventricular lumen, and strain in the left ventricle wall with routinely implemented "speckle tracking" by digital image correlation. Findings of improved fractional shortening or strain at eight weeks must be interpreted as occurring due to the combined revascularization and remuscularization therapies.

The inventors evaluate hiPSC-CM populations and engineered tissues for producing the highest quality tissues, authenticating all reagents.

LIST OF EMBODIMENTS

Specific compositions and methods of the collagen microfiber scaffolds were described. The detailed description in this specification is illustrative and not restrictive or exhaustive. The detailed description is not intended to limit the disclosure to the precise form disclosed. Other equivalents and modifications besides those already described are possible without departing from the inventive concepts described in this specification, as persons skilled in the tissue engineering art recognize. When the specification or claims recite method steps or functions in order, alternative embodiments may perform the functions in a different order or substantially concurrently. The inventive subject matter should not be restricted except in the spirit of the disclosure.

All terms should be interpreted in the broadest possible manner consistent with the context when interpreting the disclosure. Unless otherwise defined, all technical and scientific terms used in this specification have the same meaning as commonly understood by persons of ordinary skill in the tissue engineering art to which this invention belongs. This invention is not limited to the particular methodology, protocols, reagents, and the like described in this specification and can vary in practice. The terminology used in this specification is not intended to limit the scope of the invention, which is defined solely by the claims.

When a range of values is provided, each intervening value, to the tenth of the unit of the lower limit, unless the context dictates otherwise, between the upper and lower limit of that range and any other stated or intervening value in that range of values.

Some embodiments of the technology described can be defined according to the following paragraphs:

Identifying a set of growth factors/cytokines that maximize endothelial cell morphogenesis and host immune cell responses for vessel formation in vivo.

An optimum combination of growth factors/cytokines maximizes endothelial, immune, and vascular cell plasticity (migration, proliferation, and network/vessel formation) to promote angiogenesis, arteriogenesis, neovascularization, and remodeling.

Growth factor/cytokine/protein combinations are assessed in vivo, where multiple cell types can respond to the locally delivered factors for the growth and remodeling of the vascular bed.

Statistically determine potent combinations of growth factors and cytokines in a Design of Experiments approach.

Narrow down many factors to focus on significant ones and elucidate factor interactions.

IGF-1 acting individually has the strongest overall effects on multiple metrics of vascular formation: hemoglobin content, lumen density, lumen diameter, $CD31^+$ area, $\alpha SMA^+$ area, total vascular area, and vessel perfusion.

Shh alone has the second strongest overall effects on multiple metrics of vascular formation: hemoglobin content, lumen density, $CD31^+$ area, total vascular area, and vessel perfusion.

bFGF alone increases $\alpha SMA^+$ area and total vascular area.

PDGF alone increases lumen diameter.

VEGF alone increases hemoglobin content.

IGF-1 and Shh increase lumen diameter, $CD31^+$ area, and $\alpha SMA:CD31$ ratio in Matrigel's defined gel and hemoglobin content. They are the most potent cocktail in the defined alginate-collagen gel.

Shh and PDGF increase lumen diameter in both gels and increase hemoglobin content, lumen density, and vessel perfusion in Matrigel.

IGF-1 and PDGF increase hemoglobin content, $CD31^+$ area, and total vascular area.

Shh and bFGF together increase lumen diameter in the defined gel.

VEGF, bFGF, and Shh are potent for revascularization in vivo.

Histological analyses enable us to complete global analysis of these factors and their contribution to angiogenesis:

Vascular area ($CD31^+$ and $\alpha SMA^+$).

Macrophage polarization (M1/M2 ratio).

Several potent combinations of growth factors have specific and unique effects on developing new vessels and vascular beds. These features can be leveraged in different contexts to select the most appropriate factors in a cocktail for specific applications in different tissue types, diseases, and disease states (such as progressive disease) to improve vascularization and tissue perfusion.

Biomaterial fabrication process and testing of the heparinized-alginate and collagen-defined gel biomaterial.

Films made from defined biomaterial gel and their $CaCl_2$ cross-linking bath, hydrated storage, washing, and preparation for implantation.

Thin-film in paper or nylon mesh frame for mold casting and handling during surgical implantation.

Ease of trimming frame by cutting down to create rails or handles, including a single "handle" for manipulation during in vitro testing and in vivo surgical implantation.

Tensile testing of films using paper or nylon frames molds on opposite sides for strong attachment points to the testing apparatus.

Transport 'humidity chamber' with laser cut paper and nylon frame molds.

Injectable gel formulation extrusion via syringe and needle with variable gauge.

Force characterization of hydrogel extrusion via plunger force.

REFERENCES

Persons having ordinary skill in the molecular computing art can rely on the following patents, patent applications, scientific books, and scientific publications for enabling methods:

Patent Citations

U.S. Pat. No. 8,492,339B2 (Miller), Angiogenesis promoted by cage growth factors.
U.S. Pat. No. 6,759,386B2 (Franco), Methods of use of fibroblast growth factor, vascular endothelial growth factor and related proteins in the treatment of acute and chronic heart disease.
U.S. Pat. No. 7,125,856B1 (Isner), Angiogenic growth factors for treatment of peripheral neuropathy.
U.S. Pat. No. 9,675,670B2 (Clokie et al.), System and method for multiphasic release of growth factors.
US20200215228A1 (Coulombe et al.), Collagen microfiber scaffolds.
US20220163511A1 (Choi et al.), Human in vitro cardiotoxicity model.

Non-Patent Citations

Andrae et al., Role of platelet-derived growth factors in physiology and medicine. Genes & Development (2008) describes growth factor and cytokine activity in vivo.
Bella & Hulmes, Fibrillar collagens. Subcell. Biochem., 82, 457-490 (2017).
Buikema et al., Wnt activation and reduced cell-cell contact synergistically induce massive expansion of functional human iPSC-derived cardiomyocytes. Cell Stem Cell, 27(1), 50-63 e5 (2020).
Burridge et al., Chemically defined generation of human cardiomyocytes. Nature Methods, 11(8), 855-860 (2014).
de Souza Reboucas et al. Cardiac regeneration using growth factors: advances and challenges. Arq. Bras. Cardiol., 271-275 (2016).
Derakhshanfar et al., 3D bioprinting for biomedical devices and tissue engineering: a review of recent trends and advances. Bioact. Mater., 3, 144 (2018). Several approaches to emulating ECM structural and mechanical cues in 3D engineered tissues were used, including 3D printed scaffolds. 3D printed scaffolds offer high reproducibility and a broad design space, but compromises must be made in terms of either resolution or scaffold polymer, often resulting in excluding natural polymers.
Domenech et al., Tissue engineering strategies for myocardial regeneration: Acellular versus cellular scaffolds? Tissue Eng. Part B. Rev. (2016)
Elia et al., Biomaterials (2010) delivered growth factor loaded hydrogels in vivo to study combinatorial effects of VEGF, Ang-I, PDGF, and KGF on neovascularization.
Ferrara et al. The biology of VEGF and its receptors. Nature Medicine (2003) describes growth factor and cytokine activity in vivo.
Gogiraju et al. Angiogenic endothelial cell signaling in cardiac hypertrophy and heart failure. Front. Cardiovasc. Med. (2019).
Harada et al., Basic fibroblast growth factor improves myocardial function in chronically ischemic porcine hearts. J. Clin. Invest. 94(2), 623-630 (1994).
Iivarinen et al., Experimental and numerical analysis of soft tissue stiffness measurement using manual indentation device-significance of indentation geometry and soft tissue thickness. Skin Res. Technol., 20, 347 (2014).
Jafari et al., Polymeric scaffolds in tissue engineering: A literature review. J. Biomed. Mater. Res. B Appl. Biomater., 105, 431 (2017) is a literature review of polymeric scaffolds in tissue engineering. The soft tissue engineering community has used a wide variety of natural and synthetic polymer hydrogel materials as accessible scaffold materials, permitting high customization for individual uses.
Khan et al., Fibroblast growth factor and vascular endothelial growth factor play a critical role in endotheliogenesis from human adipose-derived stem cells. J. Vascular Surg. (2017) studied the role of VEGF and bFGF on angiogenesis in vitro.
Kofron et al., A predictive in vitro risk assessment platform for pro-arrhythmic toxicity using human 3D cardiac microtissues. Research Square (2021). Kofron et al., A predictive in vitro risk assessment platform for pro-arrhythmic toxicity using human 3D cardiac microtissues. Research Square (2021).
Lian et al., Directed cardiomyocyte differentiation from human pluripotent stem cells by modulating Wnt/beta-catenin signaling under fully defined conditions. Nature Protocols, 8(1), 162-175 (2013).
Liu et al., Human embryonic stem cell-derived cardiomyocytes restore function in infarcted hearts of non-human primates. Nature Biotechnol., 36(7), 597-605 (2018).
Lopez et al., Basic fibroblast growth factor in a porcine model of chronic myocardial ischemia: a comparison of angiographic, echocardiographic and coronary flow parameters. J. Pharmacol. Exp. Ther., 282(1), 385-90 (1997).
Lu et al., Mal Med. Rep. (2019) studied the combinatorial effect of VEGF and IGF-1 on human carious dental pulp stem cells and their role in angiogenesis. They concluded that the combinatorial effect of these proteins promoted angiogenesis in comparison to growth factors delivered individually.
Menasche et al., Transplantation of human embryonic stem cell-derived cardiovascular progenitors for severe ischemic left ventricular dysfunction. J. Am. Coll. Cardiol., 71(4), 429-438 (2018).
Mosadegh et al., Current progress in 3D printing for cardiovascular tissue engineering. Biomed. Mater. 10, 034002 (2015). Several approaches to emulating ECM structural and mechanical cues in 3D engineered tissues were used, including 3D printed scaffolds. 3D printed scaffolds offer high reproducibility and a broad design space, but compromises must be made in terms of either resolution or scaffold polymer, often resulting in excluding natural polymers.
Munarin et al., Engineered human myocardium with local release of angiogenic proteins improves vascularization and cardiac function in injured rat hearts. Biomaterials, 251, 120033 (2020).
Munarin et al., Heparin-modified alginate microspheres enhance neovessel formation in hiPSC-derived endothelial cells and heterocellular in vitro models by controlled release of vascular endothelial cell growth factor. J. Biomed. Mater. Res. A (2021).

Munarin et al., Laser-etched designs for molding hydrogel-based engineered tissues. Tissue Eng. Part C Methods. 23(5), 311-321 (2017) provides laser-etched designs for molding hydrogel-based engineered tissues. Stress fields resulting from tissue compaction in isometrically confined tissues are often used as a surrogate to induce cell alignment. Available methods necessitate either tissue fenestrations (reducing the efficacy and efficiency of tissues with function related to mechanics and structure) or prescribe high-aspect-ratio tissues with limited utility as a replacement tissue patches.

Neal et al., Three-dimensional elastomeric scaffolds designed with cardiac-mimetic structural and mechanical features. Tissue Eng. Part A., 19, 793 (2013).

Novosel et al., Vascularization is the key challenge in tissue engineering. Adv. Drug Delivery Rev. (2011).

Peterson & Alton, Overview of Drug Development and Statistical Tools for Manufacturing and Testing. Int. Pharm. Ind. (2016).

Pola et al. (2001) describes growth factor and cytokine activity in vivo.

Rajan et al., Nature Protocols 1, 2753 (2007) describes the preparation of ready-to-use, storable and reconstituted type I collagen from rat tail tendon for tissue engineering uses using a "twist-and-pull" method.

Raub et al., Predicting bulk mechanical properties of cellularized collagen gels using multiphoton microscopy. Acta Biomater., 6, 4657 (2010).

Romagnuolo et al., Human embryonic stem cell-derived cardiomyocytes regenerate the infarcted pig heart but induce ventricular tachyarrhythmias. Stem Cell Reports, 12(5), 967-981 (2019).

Ruel et al., Inhibition of the cardiac angiogenic response to surgical FGF-2 therapy in a Swine endothelial dysfunction model. Circulation, 108 Suppl 1, 11335-40 (2003).

Rupert et al., Human cardiac fibroblast number and activation state modulate electromechanical function of hiPSC-cardiomyocytes in engineered myocardium. Stem Cells International, 2020, U.S. Pat. No. 9,363,809 (2020).

Rupert, Irofuala, & Coulombe, Practical adoption of state-of-the-art hiPSC-cardiomyocyte differentiation techniques. PLoS One, 15(3), e0230001 (2020).

Sack et al., Intra-myocardial alginate hydrogel injection acts as a left ventricular mid-wall constraint in swine. Acta Biomater., 111, 170-180 (Jul. 15, 2020) describes a tunable delivery-specific system.

Taimeh et al. Vascular endothelial growth factor in heart failure. Nature Rev. Cardiol., 519-530 (2013).

Virani et al., Heart disease and stroke statistics-2021 update: A report from the American Heart Association. Circulation, 143(8), e254-e743 (2021).

Vo et al., The biomechanics and optimization of the needle-syringe system for injecting triamcinolone acetonide into keloids. J. Med. Eng. (2016). Voisine et al., Inhibition of the cardiac angiogenic response to exogenous vascular endothelial growth factor. Surgery, 136(2), 407-415 (2004).

Voisine et al., Inhibition of the cardiac angiogenic response to exogenous vascular endothelial growth factor. Surgery, 2004. 136(2): 407-15.

All patents and publications cited throughout this specification are expressly incorporated by reference to disclose and describe the materials and methods that might be used with the technologies described in this specification. The publications discussed are provided solely for their disclosure before the filing date. They should not be construed as an admission that the inventors may not antedate such disclosure under prior invention or for any other reason. If there is an apparent discrepancy between a previous patent or publication and the description provided in this specification, the specification (including any definitions) and claims shall control. All statements as to the date or representation as to the contents of these documents are based on the information available to the applicants and constitute no admission as to the correctness of the dates or contents of these documents. The dates of publication provided in this specification may differ from the actual publication dates. If there is an apparent discrepancy between a publication date provided in this specification and the actual publication date supplied by the publisher, the actual publication date shall control.

The invention claimed is:

1. An implantable hydrogel for promoting vascularization in an ischemic tissue of a subject in need thereof;
   the hydrogel consisting of ingredients (1), (2), (3), (4), and (5) below:
   (1) covalently bound heparinized alginate,
   (2) alginate with sterile water,
   (3) collagen,
   (4) a cross-linking agent including a buffer,
   (5) a growth factor;
   wherein the hydrogel is operative to be implanted into the subject by an injection, a subcutaneous implantation, an implantation into the tissue, or by an epicardial implantation.

2. The hydrogel of claim 1, wherein the hydrogel is made by a method comprising the steps of:
   (a) obtaining 1-4% heparin-alginate;
   (b) adding 2-6 mg/mL collagen; and
   (c) incubating in a 0.1-1.0 M $CaCl_2$ bath.

3. The hydrogel of claim 2, wherein the bath in step (c) of the method is a 0.15 M $CaCl_2$ bath.

4. The hydrogel of claim 1, wherein the hydrogel is made by a method comprising the steps of:
   (a) obtaining a 4% sodium alginate solution;
   (b) sterilizing the solution;
   (c) adding 1/10th the mass of 0.4% alginate in the heparinized form, previously functionalized with heparin and lyophilized;
   (d) combining the solution with 13 mg/mL isolated rat tail collagen and HEPES buffer;
   (e) mixing;
   (f) neutralizing the solution via the addition of NaOH until a pH of 7.0 is reached;
   (g) adding sterile $H_2O$ and/or additional growth factors to reach a target final volume;
   (h) providing final concentrations of 2% alginate, 0.2% heparinized alginate, 3 mg/mL collagen, and 1% HEPES buffer;
   (i) allowing the solution to gel;
   (j) adding the gel to a porous nylon mesh frame on a hydrophilic surface;
   (k) covering the gel on the frame with 0.15 M $CaCl_2$ for ten minutes; and
   (l) rinsing the gel in distilled phosphate-buffered saline for two minutes.

5. The hydrogel of claim 1, wherein the hydrogel is made by a method comprising the steps of:
   (a) obtaining 0.5-2% heparin-alginate;
   (b) adding 0.5-2 mg/mL collagen; and
   (c) adding 5-10 mg/mL $CaCO_3$.

6. The hydrogel of claim 1, wherein the hydrogel is made by a method comprising the steps of:
   (a) obtaining a 2% alginate solution including dissolved therein 0.2% lyophilized heparinized alginate;
   (b) combining the solution with 13 mg/mL isolated rat tail collagen to produce a concentration of 1% heparinized alginate;
   (c) adding sterile H2O and/or additional growth factors;
   (d) mixing;
   (e) mixing a $CaCO_3$ solution in a remaining available volume to produce a concentration of 5 mg/mL $CaCO_3$; and
   (f) loading the hydrogel mixture from step (e) into a syringe.

7. The hydrogel of claim 1, wherein the growth factor further is sonic hedgehog (Shh).

8. The hydrogel of claim 1, wherein the growth factor is selected from the group consisting of VEGF, bFGF, Shh, PDGF, IGF-1, and a combination thereof.

9. The hydrogel of claim 1, wherein the hydrogel is in a form of a thin film.

10. The hydrogel of claim 1, wherein the hydrogel is in a form of an injected gel.

11. An implantable hydrogel for promoting vascularization in an ischemic tissue of a subject in need thereof;
   the hydrogel consisting of ingredients (1), (2), (3), and (4) below:
   (1) covalently bound heparinized alginate,
   (2) alginate with sterile water,
   (3) collagen,
   (4) a cross-linking agent including a buffer;
   wherein the hydrogel is operative to provide a vehicle for a growth factor and is operative to be implanted into the subject by an injection, a subcutaneous implantation, an implantation into the tissue, or by an epicardial implantation.

12. The hydrogel of claim 1 or claim 11, wherein the buffer is selected from the group consisting of $CaCO_3$, $CaCl_2$, NaOH, HEPES, phosphate-buffered saline, and a combination thereof.

* * * * *